United States Patent
Sarek et al.

(10) Patent No.: US 8,653,056 B2
(45) Date of Patent: Feb. 18, 2014

(54) METHOD OF PREPARATION OF A SOLUBLE FORMULATION OF WATER-INSOLUBLE PENTACYCLIC AND TETRACYCLIC TERPENOIDS, A SOLUBLE FORMULATION OF A PENTACYCLIC OR TETRACYCLIC TERPENOID AND A PHARMACEUTICAL COMPOSITION CONTAINING THIS SOLUBLE FORMULATION

(75) Inventors: Jan Sarek, Horni Mecholupy (CZ); Marian Hajduch, Moravsky Beroun (CZ); Michal Svoboda, Praha (CZ); Katerina Novakova, Kladno (CZ); Pavla Spacilova, Ostrava (CZ); Tomas Kubelka, Praha (CZ); David Biedermann, Praha (CZ)

(73) Assignees: Univerzita Karlova V Praze, Prirodovedecka Fakulta, Praha (CZ); Univerzita Palackeho V Olomouci, Olomouc (CZ); I.Q.A., A.S., Praha (CZ)

( * ) Notice: Subject to any disclaimer, the term of this patent is extended or adjusted under 35 U.S.C. 154(b) by 676 days.

(21) Appl. No.: 12/443,304

(22) PCT Filed: Sep. 25, 2007

(86) PCT No.: PCT/CZ2007/000088
§ 371 (c)(1),
(2), (4) Date: Apr. 10, 2009

(87) PCT Pub. No.: WO2008/037226
PCT Pub. Date: Apr. 3, 2008

(65) Prior Publication Data
US 2009/0325919 A1   Dec. 31, 2009

(30) Foreign Application Priority Data
Sep. 27, 2006  (CZ) .................... 2006-606

(51) Int. Cl.
*A61K 31/56* (2006.01)
*C07J 1/00* (2006.01)

(52) U.S. Cl.
USPC ............ 514/179; 514/182; 552/612; 552/623

(58) Field of Classification Search
USPC ........................ 514/179, 182; 552/612, 623
See application file for complete search history.

(56) References Cited

U.S. PATENT DOCUMENTS

2005/0239748 A1* 10/2005 Power et al. ............... 514/58
2006/0194774 A1*  8/2006 Selzer et al. ................ 514/169

* cited by examiner

*Primary Examiner* — Paul Zarek
(74) *Attorney, Agent, or Firm* — Notaro, Michalos & Zaccaria P.C.

(57) ABSTRACT

The invention relates to a method of preparation of a soluble formulation of water-insoluble pentacyclic and tetracyclic terpenoids, wherein the water-insoluble terpenoid having a free carboxylic, hydroxy or amino functional group is derivatized on this functional group with a substituent selected from the group comprising substituents of general formula Xa bound to the hydroxy group of the terpenoid, wherein Xa is —OC—R—COOH, substituents of general formula Xa bound to the amino group of the terpenoid, wherein Xa is —OC—R—COOH, quarternary ammonium substituents of general formula Xb bound to the carboxy group of the terpenoid, wherein Xb is —(CH2)nN+R3Y—, quarternary ammonium substituents of general formula Xc bound to the carboxy group of the terpenoid, wherein Xc je —(CH2)nR+Y—, substituents of general formula Xd bound to the carboxy group of the terpenoid, wherein Xd represents —R—COOH, glycosylic substituents Xe bound by alpha or beta glycosidic bond to the hydroxy group or to the carboxy group of the terpenoid, wherein Xe is selected from the group comprising glucosyl, galactosyl, arabinosyl, rhamnosyl, lactosyl, cellobiosyl, maltosyl and the 2-deoxyanalogues thereof, and subsequently, the prepared derivative is dissolved in the solution containing water, a cyclodextrin and optionally pharmaceutically acceptable auxiliary substances, forming an inclusion derivative with the cyclodextrin. Object of the invention is further a soluble formulation of a pentacyclic or tetracyclic triterpenoid, containing an inclusion complex of the derivatized pentacyclic or tetracyclic terpenoid with a cyclodextrin, and optionally water and pharmaceutically acceptable auxiliary substances and further a pharmaceutical composition containing the soluble formulation.

6 Claims, 4 Drawing Sheets

Fig. 1: Pharmacokinetic profile of the hemisuccinate 2b at oral administration to mice
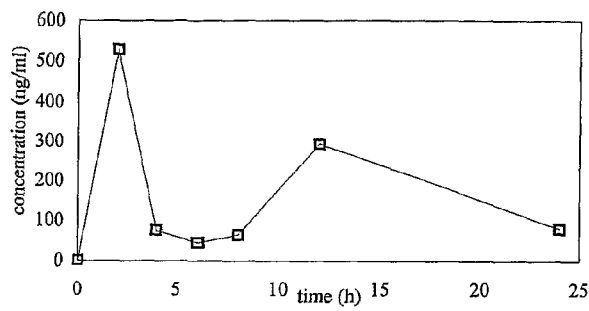
Fig. 2: Pharmacokinetic profile of the aldehyde 3 at oral administration to mice
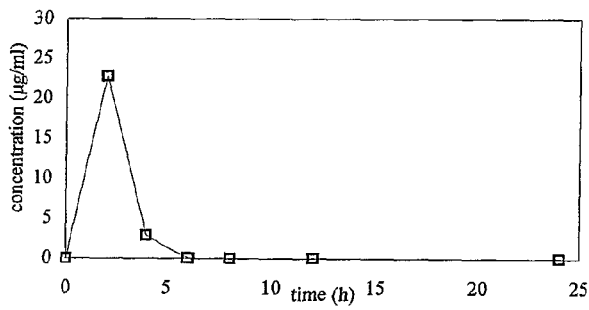
Fig. 3: Pharmacokinetic profile of the hemisuccinate 3b at oral administration to mice
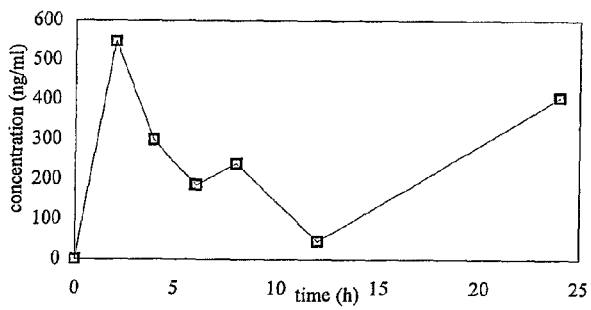

Fig. 4: Pharmacokinetic profile of the hemisuccinate 5a at oral administration to mice
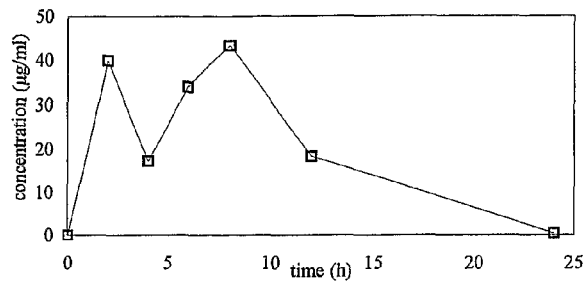
Fig. 5: Pharmacokinetic profile of the diketone-dihemisukcinate 5e at oral administration to mice
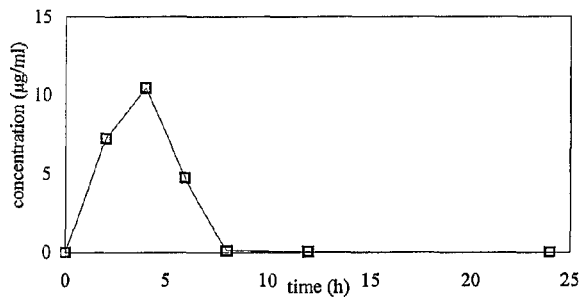
Fig. 6: Pharmacokinetic profile of the pyrazine 6a at oral administration to mice
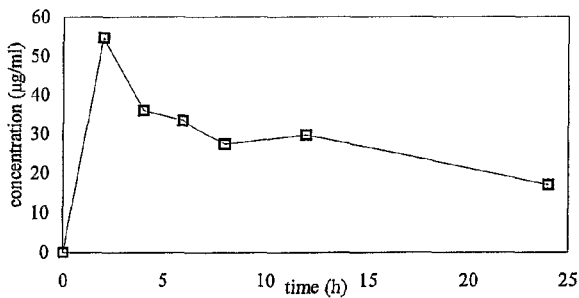

Fig. 7: Pharmacokinetic profile of the hemisuccinate 8a at oral administration to mice
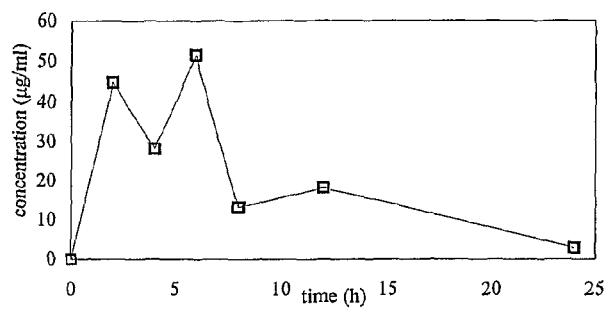
Fig. 8: Pharmacokinetic profiles of compounds 5c, 5d, 6, 7, 8 administered in the form of suspension with carboxymethyl cellulose orally to mice.
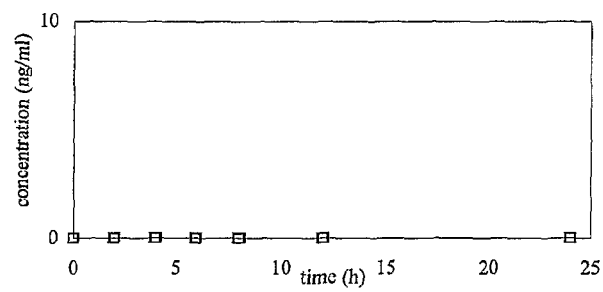
Fig. 9: Pharmacokinetic profile of the 2-deoxygalactoside 4v at oral administration to mice
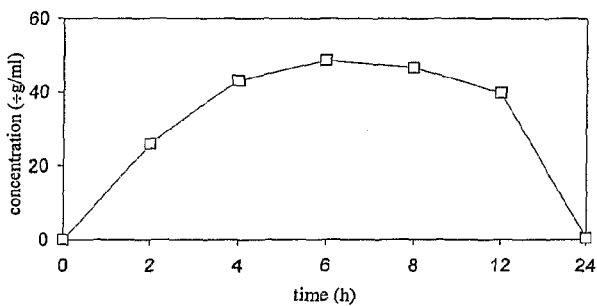

Fig. 10: Pharmacokinetic profile of the glucoside 4i at oral administration to mice
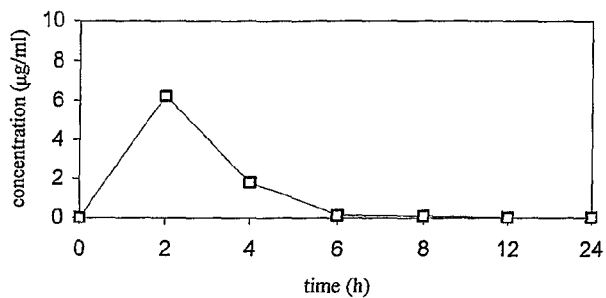
Fig. 11: Pharmacokinetic profile of the hemiglutarate 2i at oral administration to mice
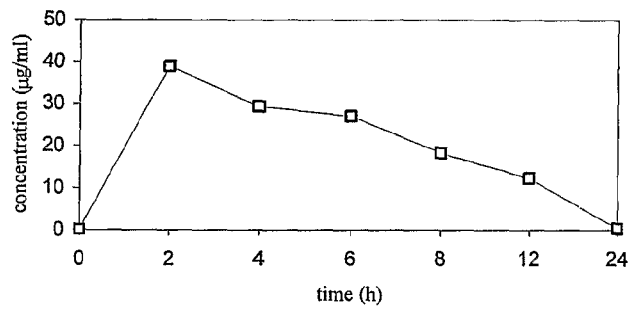
Fig. 12: Pharmacokinetic profile of the 3′,3′-dimethylhemisuccinate 4t at oral administration to mice
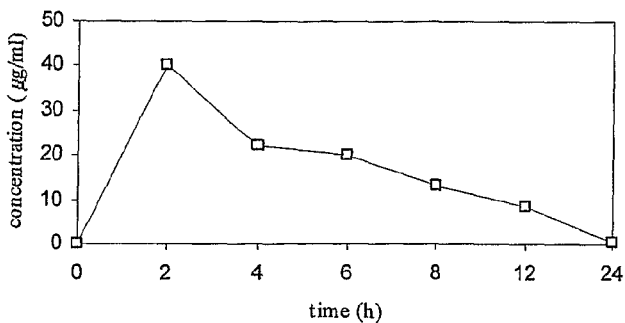

METHOD OF PREPARATION OF A SOLUBLE FORMULATION OF WATER-INSOLUBLE PENTACYCLIC AND TETRACYCLIC TERPENOIDS, A SOLUBLE FORMULATION OF A PENTACYCLIC OR TETRACYCLIC TERPENOID AND A PHARMACEUTICAL COMPOSITION CONTAINING THIS SOLUBLE FORMULATION

The application claims priority from international application number PCT/CZ2007/000088, filed Sep. 25, 2007, which claims priority from Czech Re-public Application No. PV2006-606, filed Sep. 25, 2006, which priority claim is repeated here.

TECHNICAL FIELD

The invention relates to a method of preparation of a soluble formulation of water-insoluble pentacyclic and tetracyclic terpenoids, a soluble formulation of a pentacyclic or tetracyclic terpenoid and a pharmaceutical composition containing this soluble formulation.

BACKGROUND ART

Pentacyclic and tetracyclic terpenoids represent a group of natural substances—isoprenoids, showing a large range of biological activities (Dzubak, P.; Hajduch, M.; Vydra, D.; Hustova, A.; Kvasnica, M.; Biedermann, D.; Markova, L.; Urban, M.; Sarek, J. Nat. Prod. Rep. 2006, 23, 394-411), thanks to which they are getting into the focus of the pharmaceutical industry. However, neither modified nor semisynthetic derivatives of these natural substances possess optimum pharmacological properties. Among their disadvantages belong namely low solubility in water-based media and further disadvantageous pharmacokinetic indicators such as low biological availability, short half-time of excretion and insufficient stability, which are unsuitable for carrying out in vivo tests in animals as well as for subsequent use in treatment of patients.

The pentacyclic and tetracyclic terpenoids are almost water-insoluble, since they have rigid lipophilic skeleton, composed of 25-30 carbon atoms, even if they bear polar functional groups such as —OH, —COOH, =O, —$NH_2$ etc. The solvents commonly used in the chemical practice, such as chloroform, acetone, ethyl acetate etc., cannot be used for dissolving for pharmaceutical purposes, for the reason of their incompatibility with living organisms. In the art it is known that in the presence of alkali carbonates or hydrogencarbonates, pentacyclic triterpenoid acids form inclusion compounds with cyclodextrins, these inclusion compounds being soluble in water-based media with the addition of suitable additives (WO 92/09553). It is taught that the highest solubility of triterpenoid acids can be achieved with the use of higher cyclodextrins, namely β and γ, and lower alcohols (methanol) or glycols (propylene glycol, butandiol) are used as additives (Uekama K., Hirayama F., Irie T.: Chem. Rev. 1998, 98, 2045-2076, Hedges A. R.: Chem. Rev. 1998, 98, 2035-2044). In the vehicles used, the triterpenoids reach the solubility between 10 and 50 mg/ml (WO 92/09553). The inclusion compounds can be isolated from their solutions as solid substances in the form of powder by means of lyophilization. However, only native triterpenoid carboxylic acids having a free carboxylic functional group can be dissolved in water-based media, but not their functional derivatives or terpenoids that do not have carboxylic functional group. Furthermore, in the pharmaceutical practice, the biologically active free triterpenoid acids, having many disadvantageous pharmacological properties, e.g. difficult purificability and instability, are often converted into derivatives bringing often a slower metabolization (increase of the half-life), increase of stability or functioning as prodrug. One type of these derivatives are various biologically cleavable esters, such as e.g. morpholinoethyl esters, acetoxymethyl esters, heptyl esters etc. (Gewehr M., Kunz H.: Synthesis 1997, 1499; Urban M., Sarek J., Tislerova I., Dzubak P., Hajduch M.: Bioorg. Med. Chem. 2005, 13, 5527)

In general, the carboxylic acid derivatives are even less compatible with water-based vehicles than the free acids. For the exploitation of the carboxylic acid derivatives in the pharmaceutical practice, it is necessary to find a formulation enabling their use with the water-based vehicles.

From the above given reasons it is clear that for further development, it is necessary to prepare the derivatives of the insoluble biologically active pentacyclic and tetracyclic terpenoids that are soluble in water-based media, are bioavailable (preferably orally available), have a suitable half-time of excretion and are stable, i.e. that have optimum pharmacokinetic parameters.

DISCLOSURE OF INVENTION

Object of the invention is a method of preparation of a soluble formulation of water-insoluble pentacyclic and tetracyclic terpenoids, wherein the water-insoluble terpenoid having a free carboxylic, hydroxy or amino functional group is derivatized on this functional group with a substituent selected from the group comprising a) substituents of general formula $X^a$ bound to the hydroxy group of the terpenoid, wherein $X^a$ is —OC—R—COOH, wherein R is linear or branched $C_1$ to $C_8$ alkylene, linear or branched $C_3$ to $C_8$ oxaalkylene, linear or branched $C_1$ to $C_8$ alkenylene, $C_6$ cycloalkylene, $C_6$ cycloalkenylene, $C_6$ arylene unsubstituted or substituted with halogen, hydroxyl or amino group:

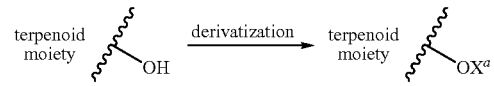

b) substituents of general formula $X^a$ bound to the amino group of the terpenoid, wherein $X^a$ is —OC—R—COOH, wherein R is linear or branched $C_1$ to $C_8$ alkylene, linear or branched $C_3$ to $C_8$ oxaalkylene, linear or branched $C_1$ to $C_8$ alkenylene, $C_6$ cycloalkylene, $C_6$ cycloalkenylene, $C_6$ arylene unsubstituted or substituted with halogen, hydroxyl or amino group:

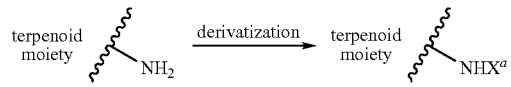

c) quarternary ammonium substituents of general formula $X^b$ bound to the carboxy group of the terpenoid, wherein $X^b$ is —$(CH_2)_n N^+ R_3 Y^-$, wherein n is 2-8, R is linear or branched $C_1$ to $C_8$ alkyl, optionally substituted with —OH, —$NH_2$ or halogen, and $Y^-$ is anion selected from the group comprising halogenide, sulphate, hydrogensulphate and triflate:

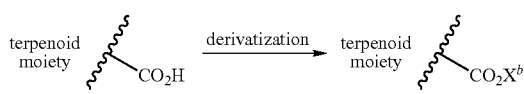

d) quarternary ammonium substituents of general formula $X^c$ bound to the carboxy group of the terpenoid, wherein $X^c$ je —$(CH_2)_nR^+Y^-$, wherein n is 2-8, $R^+$ is protonated nitrogen-containing heterocycle containing 1-2 nitrogen atoms and 4-9 carbon atoms and containing at least one aromatic cycle and $Y^-$ is anion selected from the group comprising halogenide, sulphate, hydrogensulphate and triflate:

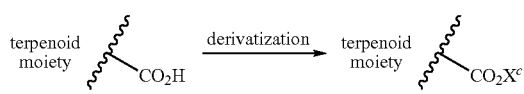

e) substituents of general formula $X^d$ bound to the carboxy group of the terpenoid, wherein $X^d$ represents —R—COOH, wherein R is linear or branched $C_1$ to $C_4$ alkylene, linear or branched $C_1$ to $C_4$ alkenylene, $C_6$ arylene unsubstituted or substituted with halogen, hydroxy or amino group:

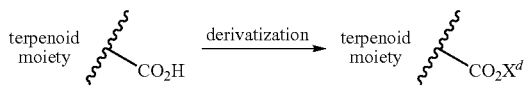

f) glycosylic substituents $X^e$ bound by α or β glycosidic bond to the carboxy group of the terpenoid, wherein $X^e$ is selected from the group comprising glucosyl, galactosyl, arabinosyl, rhamnosyl, lactosyl, cellobiosyl, maltosyl and the 2-deoxyanalogues thereof:

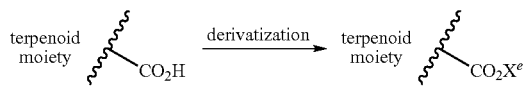

g) glycosylic substituents $X^e$ bound by α or β glycosidic bound to the hydroxy group of the terpenoid, wherein $X^e$ is selected from the group comprising glucosyl, galactosyl, arabinosyl, rhamnosyl, lactosyl, cellobiosyl, maltosyl and the 2-deoxyanalogues thereof:

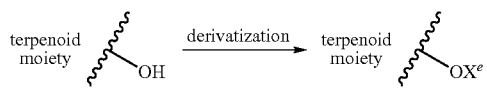

and subsequently, the prepared derivative is dissolved in a solution containing water, a cyclodextrin and optionally pharmaceutically acceptable auxiliary substances, forming an inclusion derivative with the cyclodextrin.

In a preferred embodiment of the invention, the substituents of general formula Xa are selected from the group comprising succinate, glutarate, 3',3'-dimethylglutarate, 3',3'-dimethylsuccinate, tetrahydrophthalate, diglycolate or phthalate.

In a preferred embodiment of the invention, the substituents of general formula $X^b$ are choline esters, wherein n=2, $R=CH_3$.

In a preferred embodiment of the invention, the substituents of general formula $X^c$ are pyridinium salts, wherein n=2, $R^+=PyH^+$, $Y^-=Br^-$.

In a preferred embodiment of the invention, the substituents of general formula $X^d$ are glycolates, wherein $R=CH_2$.

In a preferred embodiment of the invention, the substituents of general formula $X^e$ are selected from the group comprising glucosyl, galactosyl, lactosyl and the 2-deoxyanalogues thereof.

In a preferred embodiment of the invention, the cyclodextrin is selected from the group comprising native or substituted β-cyclodextrins and γ-cyclodextrins.

Biocompatible organic solvents, e.g. ethanol or propylene glycol, and compounds facilitating the formation of inclusion complexes, such as e.g. alkali carbonates or hydrogen carbonates can be the auxiliary substances.

Object of the invention is further a soluble formulation of a pentacyclic or tetracyclic triterpenoid, containing an inclusion complex of the pentacyclic or tetracyclic terpenoid having its carboxy, hydroxy or amino group derivatized with a substituent selected from the group comprising:
  a) substituents of general formula $X^a$ bound to the hydroxy group of the terpenoid, wherein $X^a$ is —OC—R—COOH, wherein R is linear or branched $C_1$ to $C_8$ alkylene, linear or branched $C_3$ to $C_8$ oxaalkylene, linear or branched $C_1$ to $C_8$ alkenylene, $C_6$ cycloalkylene, $C_6$ cycloalkenylene, $C_6$ arylene unsubstituted or substituted with halogen, hydroxyl or amino group;
  b) substituents of general formula $X^a$ bound to the amino group of the terpenoid, wherein $X^a$ is —OC—R—COOH, wherein R is linear or branched $C_1$ to $C_8$ alkylene, linear or branched $C_3$ to $C_8$ oxaalkylene, linear or branched $C_1$ to $C_8$ alkenylene, $C_6$ cycloalkylene, $C_6$ cycloalkenylene, $C_6$ arylene unsubstituted or substituted with halogen, hydroxyl or amino group;
  c) quarternary ammonium substituents of general formula $X^b$ bound to the carboxy group of the terpenoid, wherein $X^b$ is —$(CH_2)_nN^+R_3Y^-$, wherein n is 2-8, R is linear or branched $C_1$ to $C_8$ alkyl, optionally substituted with —OH, —$NH_2$ or halogen, and $Y^-$ is anion selected from the group comprising halogenide, sulphate, hydrogensulphate and triflate;
  d) quarternary ammonium substituents of general formula $X^c$ bound to the carboxy group of the terpenoid, wherein $X^c$ je —$(CH_2)_nR+Y$—, wherein n is 2-8, $R^+$ is protonated nitrogen-containing heterocycle containing 1-2 nitrogen atoms and 4-9 carbon atoms and containing at least one aromatic cycle and $Y^-$ is anion selected from the group comprising halogenide, sulphate, hydrogensulphate and triflate;
  e) substituents of general formula $X^d$ bound to the carboxy group of the terpenoid, wherein $X^d$ represents —R—COOH, wherein R is linear or branched $C_1$ to $C_4$ alkylene, linear or branched $C_1$ to $C_4$ alkenylene, $C_6$ arylene unsubstituted or substituted with halogen, hydroxy or amino group;
  f) glycosylic substituents $X^e$ bound by α or β glycosidic bound to the carboxy group of the terpenoid, wherein $X^e$ is selected from the group comprising glucosyl, galactosyl, arabinosyl, rhamnosyl, lactosyl, cellobiosyl, maltosyl and the 2-deoxyanalogues thereof;
  g) glycosylic substituents $X^e$ bound by α or β glycosidic bound to the hydroxy group of the terpenoid, wherein $X^e$ is selected from the group comprising glucosyl, galactosyl, arabinosyl, rhamnosyl, lactosyl, cellobiosyl, maltosyl and the 2-deoxyanalogues thereof, with a cyclodextrin, and optionally water and pharmaceutically acceptable auxiliary substances.

In a preferred embodiment of the invention, the substituents of general formula $X^a$ are selected from the group comprising succinate, glutarate, 3',3'-dimethylsuccinate, 3',3'-dimethylglutarate, tetrahydrophthalate, diglycolate or phthalate.

In a preferred embodiment of the invention, the substituents of general formula $X^b$ are choline esters, wherein n=2, R=CH$_3$.

In a preferred embodiment of the invention, the substituents of general formula $X^c$ are pyridinium salts, wherein n=2, $R^+$=PyH$^+$, $Y^-$=Br$^-$.

In a preferred embodiment of the invention, the substituents of general formula $X^d$ are glycolates, wherein R=CH$_2$.

In a preferred embodiment of the invention, the substituents of general formula $X^e$ are selected from the group comprising glucosyl, galactosyl, lactosyl and the 2-deoxyanalogues thereof.

In a preferred embodiment of the invention, the cyclodextrin is selected from the group comprising native or substituted β-cyclodextrins and γ-cyclodextrins.

Biocompatible organic solvents, e.g. ethanol or propylene glycol, and compounds facilitating the formation of inclusion complexes, such as e.g. alkali carbonates or hydrogen carbonates can be the auxiliary substances.

Object of the invention is further a pharmaceutical composition containing the soluble formulation according to the present invention and a pharmaceutically acceptable solvent.

In a preferred embodiment according to the invention, the pharmaceutically acceptable solvent is water.

FIGURES

FIG. 1 represents the pharmacokinetic profile of the hemisuccinate 2b, administered in the form of aqueous solution of the inclusion complex with 2-hydroxypropyl-γ-cyclodextrin at the oral administration to mice.

FIG. 2 represents the pharmacokinetic profile of the aldehyde 3, administered in the form of aqueous solution of the inclusion complex with 2-hydroxypropyl-ycyclodextrin at the oral administration to mice.

FIG. 3 represents the pharmacokinetic profile of the hemisuccinate 3b, administered in the form of aqueous solution of the inclusion complex with 2-hydroxypropyl-γ-cyclodextrin at the oral administration to mice.

FIG. 4 represents the pharmacokinetic profile of the hemisuccinate 5a, administered in the form of aqueous solution of the inclusion complex with 2-hydroxypropyl-γ-cyclodextrin at the oral administration to mice.

FIG. 5 represents the pharmacokinetic profile of the diketone-dihemisuccinate 5e, administered in the form of aqueous solution of the inclusion complex with 2-hydroxypropyl-γ-cyclodextrin at the oral administration to mice.

FIG. 6 represents the pharmacokinetic profile of the pyrazine 6a, administered in the form of aqueous solution of the inclusion complex with 2-hydroxypropyl-γ-cyclodextrin at the oral administration to mice.

FIG. 7 represents the pharmacokinetic profile of the hemisuccinate 8a, administered in the form of aqueous solution of the inclusion complex with 2-hydroxypropyl-γ-cyclodextrin at the oral administration to mice.

FIG. 8 represents the pharmacokinetic profiles of the compounds 5c, 5d, 6, 7, 8 administered in the form of suspension with carboxymethyl cellulose (CMC) orally to mice.

FIG. 9 represents the pharmacokinetic profile of the 2-deoxygalactoside 4v at oral administration to mice.

FIG. 10 represents the pharmacokinetic profile of the glucoside 41 at oral administration to mice.

FIG. 11 represents the pharmacokinetic profile of the hemiglutarate 21 at oral administration to mice.

FIG. 12 represents the pharmacokinetic profile of the 3',3'-dimethylhemisuccinate 4t at oral administration to mice.

EXAMPLES

The method of preparation of the soluble formulations of water-insoluble pentacyclic and tetracyclic terpenoids consists of two steps: a) derivatization of the insoluble starting compound, b) preparation of the aqueous solution of the inclusion complex of the derivative and cyclodextrine.

All compounds described in the examples and their evaluated properties are summarized in Table 1 and represented in formulas 1 to 8.

The general methods of derivatization of the insoluble pentacyclic and tetracyclic triterpenoids are designated H-1, H-1*, H-2, H-3, H-4, H-5, H-6, H-6*, H-7, H-7*, H-8, H-9, K-1, K-2, K-3 and are herein below demonstrated in specific examples. Method designations without asterisk stand for direct derivatization methods, whereas method designations with asterisk stand for derivatization methods going via benzylester of triterpenic acid and leading to derivatives with two free carboxylic groups—one formed by the derivatization and the other being skeletal carboxylic group. The general methods of the preparation of the inclusion complex, comprising the dissolution of the substance, are designated A and B.

a) Derivatization of the Insoluble Substance

Example 1

Preparation of Betulin-Dihemisuccinate (1a)
(Method H-1)

Into a solution of betulin (1) (500 mg; 1.13 mmol) in pyridine (20 ml), succinic anhydride (1.2 g; 12.0 mmol) and N,N-dimethylaminopyridine, hereinafter DMAP (1.2 g; 10.0 mmol), were added and the reaction mixture was refluxed under stirring for 12 h. The course of the reaction was monitored by thin-layer chromatography, hereinafter TLC (hexane/ethyl acetate 1:1). The reaction mixture was then cooled down, diluted with ten-fold excess of water and extracted into ethyl acetate. Combined organic phases were shaken three times with 5% HCl, three times with water, dried with magnesium sulphate and the solvents were vacuum-dried at a rotary vacuum evaporator. The evaporate was purified by column chromatography on silica gel by gradient elution from 20% ethyl acetate in hexane to 100% ethyl acetate. The chromatographically uniform dihemisuccinate 1a was lyophilised from tert-butyl alcohol. The obtained hemisuccinate 1a (387 mg; 67%) had the melting point 107° C., [α]$_D$=10° (c=0.44). $^{13}$C NMR spectrum: 14.8, 16.0, 16.1, 16.5, 18.1, 19.1, 20.8, 23.6, 25.2, 27.0, 27.9, 29.0, 29.0, 29.1, 29.3, 29.5, 29.6, 34.1, 34.4, 37.0, 37.6, 37.8, 38.4, 40.9, 42.7, 46.4, 47.7, 48.8, 50.3, 55.4, 63.2, 81.5, 109.9, 150.1, 171.8, 172.4, 177.8, 177.8.

Example 2

Preparation of Hemisuccinate 5a (Method H-1)

Into a solution of hydroxydiketone 5 (500 mg; 1.0 mmol) in the mixture of pyridine (15 ml) and tetrahydrofurane, hereinafter THF (5 ml), succinic anhydride (900 mg; 9.0 mmol) and DMAP (982 mg; 8.0 mmol) were added and the reaction mixture was refluxed under stirring for 12 h. The course of the reaction was monitored by TLC (hexane/ethyl acetate 1:1). The reaction mixture was then cooled down and worked-up analogically as in the preparation of the compound 1a. The chromatographically uniform hemisuccinate 5a was crystallized from the mixture acetonitrile/water. The obtained hemisuccinate 5a (383 mg; 64%) had the m.p. 154-157° C., $[\alpha]_D=-99°$ (c=0.24). $^{13}$C NMR spectrum: 16.1, 16.5, 16.7, 16.8, 18.0, 19.7, 19.8, 21.0, 23.5, 25.9, 27.4, 27.8, 27.9, 28.4, 28.9, 29.2, 34.5, 37.1, 37.8, 38.5, 41.5, 45.5, 46.1, 50.8, 50.8, 53.4, 55.4, 81.2, 150.6, 168.1, 171.0, 171.9, 177.6, 189.2, 194.3.

Example 3

Preparation of Hemisuccinate 8a (Method H-1)

Into a solution of amino alcohol 8 (500 mg; 1.1 mmol) in tetrahydrofurane (10 ml), succinic anhydride (900 mg; 9.0 mmol) was added and the reaction mixture was refluxed under stirring for 5 h. The course of the reaction was monitored by TLC (hexane/ethyl acetate 1:1). The reaction mixture was then cooled down and worked-up analogically as in the preparation of the compound 1a. The chromatographically uniform hemisuccinate 8a was crystallized from the mixture acetonitrile/water. The obtained hemisuccinate 8a (406 mg; 67%) had m.p. 283-284° C., $[\alpha]_D=+65°$ (c=0.34).

Example 4

Preparation of Free Acid Hemisuccinate 2e (Method H-1*)

To a mixture of betulinic acid (2) (500 mg; 1.1 mmol) and potassium carbonate (276 mg; 2.0 mmol) in N,N-dimethylformamide, hereinafter DMF (20 ml), benzylbromide (178 µl; 1.5 mmol) was added and the reaction mixture was stirred at room temperature for 24 h. The course of the reaction was monitored by TLC (toluene/diethyl ether 10:1). The reaction mixture was then diluted with ten-fold excess of water and extracted into ethyl acetate. Combined organic phases were shaken three times with 5% HCl, three times with water, dried with magnesium sulphate and the solvents were evaporated at a rotary vacuum evaporator. The evaporate was purified by column chromatography on silica gel, toluene being the mobile phase. The obtained crude benzyl betulinate (517 mg; 86%) was used without purification in the next step.

To a solution of benzyl betulinate (500 mg; 0.9 mmol) in pyridine (20 ml), succinic anhydride (900 mg; 9.0 mmol) and DMAP (982 mg; 8.0 mmol) were added and the reaction mixture was refluxed under stirring for 15 h. The course of the reaction was monitored by TLC (hexane/ethyl acetate 1:1). The reaction mixture was then cooled down, diluted with ten-fold excess of water and extracted into ethyl acetate. Combined organic extracts were shaken three times with 5% HCl, three times with water, dried with magnesium sulphate and the solvents were evaporated at a rotary vacuum evaporator. The evaporate was purified by column chromatography on silica gel by gradient elution from 10% ethyl acetate in hexane to 50% ethylacetate. The chromatographically uniform benzyl betulinate hemisuccinate was used in the next step without purification.

To a solution of benzyl betulinate hemisuccinate (389 mg; 0.6 mmol) in the mixture of tetrahydrofurane (10 ml) and methanol (5 ml) palladium on carbon (50 mg; 10%) and 1,4-cyclohexadiene (568 µl; 6 mmol) were added and the reaction mixture was stirred at room temperature for 22 h. The course of the reaction was monitored by TLC (hexane/ethyl acetate 1:1). The reaction mixture was then filtered through diatomaceous earth and the eluate was evaporated at a rotary vacuum evaporator. By the crystallization of the evaporate from benzene, hemisuccinate 2e (366 mg; 91%) having m.p. 265° C., $[\alpha]_D=15°$ (c=0.37) was obtained. $^{13}$C NMR spectrum: 14.6, 16.2, 16.2, 16.6, 18.2, 19.3, 20.9, 23.6, 25.4, 28.0, 29.2, 29.4, 29.7, 30.5, 32.1, 34.1, 37.1, 37.1, 37.9, 38.2, 38.4, 40.7, 42.4, 46.9, 49.2, 50.2, 55.3, 56.5, 81.5, 109.7, 150.3, 171.7, 178.3, 182.7.

Example 5

Preparation of Hemiphthalate 2c (Method H-2)

To a solution of ethyl betulinate (2a) (500 mg; 1.0 mmol) in pyridine (20 ml) phthalic anhydride (1.48 g; 10.0 mmol) and DMAP (366 mg; 3.0 mmol) were added and the reaction mixture was refluxed under stirring for 28 h. The course of the reaction was monitored by TLC (hexane/ethyl acetate 1:1). The reaction mixture was then cooled down and worked up and the product was purified analogically as in the preparation of the compound 1a. The chromatographically uniform hemiphthalate 2c was lyophilized from tert-butyl alcohol. The obtained hemiphthalate 2c (335 mg; 53%) had m.p. 131° C., $[\alpha]_D=26°$ (c=0.45).

Example 6

Preparation of Betuline Dihemiphthalate (1b) (Method H-2)

To a solution of betuline (1) (500 mg; 1.13 mmol) in pyridine (20 ml), phthalic anhydride (1.33 g; 9.0 mmol) and DMAP (366 mg; 3.0 mmol) were added and the reaction mixture was refluxed under stirring for 37 h. The course of the reaction was monitored by TLC (hexane/ethyl acetate 1:1). The reaction mixture was then cooled down and worked up and the product was purified analogically as in the preparation of the compound 1a. The chromatographically uniform dihemiphthalate 1b was lyophilized from tert-butyl alcohol. The obtained dihemiphthalate 1b (633 mg; 76%) had m.p. 178-180° C., $[\alpha]_D=28°$ (c=0.55).

Example 7

Preparation of Glucoside 4i (Method H-3)

i) To a solution of ethylester 4g (1.00 g; 2.07 mmol) in dry acetonitrile (25 ml) 2,3,4,6-tetraacetyl-α-D-glucopyranosyl bromide (1.7 g; 4.1 mmol) and mercury cyanide (782 mg; 3.1 mmol) and the mixture was then refluxed under reflux condenser with the exclusion of air moisture. The course of the reaction was monitored by TLC (toluene/ether 6:1). The cooled-down reaction mixture was then bubbled through with moist hydrogensulphide, filtered through diatomaceous earth, the filtrate was diluted with ten-fold excess of water and extracted into ethyl acetate. Combined organic extracts were shaken three times with water, dried with magnesium sulphate and the solvents were evaporated at a rotary vacuum evaporator. The evaporate was purified by column chromatography on silica gel, toluene with diethyl ether gradient being the mobile phase. The obtained acetylated glucoside 4h (550 mg; 33%) had m.p. 110° C., $[\alpha]_D=-33°$ (c=0.32). IR spectrum: 1246 (C—O); 1609 (C=C); 1697, 1754 (C=O). $^1$H NMR spectrum: 0.73 s, 3H; 0.87 s, 3H; 0.90 s, 3H; 0.92 s, 3H, 1.02 s, 3H, 1.20 s, 3H; 1.22 s, 3H; (7×CH$_3$); 1.26 t, 3H (J=7.4; —CH$_2$—CH$_3$); 2.01 s, 3H; 2.03 s, 3H, 2.04 s, 3H, 2.09 s, 3H (4×CH$_3$COO); 2.46 d, 1H (J=18.6; H-22b); 2.46 m, 1H (ΣJ=12.0; H-16β); 2.68 dd, 1H (J$_1$=12.7, J$_2$=3.2; H-13β); 3.08 m, 1H, (ΣJ=16.4; H-3α); 3.20 septet, 1H (J=7.1; H-20); 3.69 m, 1H (J=20.0; H-5'); 4.10-4.28 m, 4H(O—CH$_2$, H-6'a,b); 4.54 d, 1H (J=8.1; H-1'); 5.01-5.09 m, 2H(H-4', H-2'); 5.18-5.24 m, 1H (ΣJ=24; H-3'). MS ESI m/z (%): [For C$_{46}$H$_{64}$O$_{13}$, M$^+$ 828], 829 ([M+H]$^+$, 10); (851 ([M+Na]$^+$, 40). Elemental analysis for C$_{46}$H$_{64}$O$_{13}$: calculated C, 66.64%, H, 8.27%; found C, 61.97%, H, 8.12%.

ii) The obtained acetylated glucoside 4h (330 mg; 0.39 mmol) was mixed with dry methanol (10 ml) and metal sodium (5 mg) was added. The course of the reaction was monitored by reverse TLC (water/THF 1:1). The reaction mixture was then acidified with acetic acid to pH 6 and evaporated at a rotary vacuum evaporator. Water was added to the evaporate and the resulting suspension was drained out and washed with water. The precipitate was dried in exsiccator over phosphorus(V) oxide. The obtained free glucoside 4i (180 mg; 0.28 mmol), 68%) had m.p. 196.0° C., [α]$_D$=−46° (c=0.29). IR spectrum: 1609 (C=C); 1697, 1724 (C=O); 3411 (O—H). $^1$H NMR spectrum: 0.82 s, 3H; 0.89 s, 3H; 0.93 s, 3H, 1.02 s, 3H, 1.03 s, 3H, 1.20 s, 3H, 1.21 s, 3H (7×CH$_3$); 1.25 t, 3H (J=7.2; —CH$_2$—CH$_3$); 2.14 d, 1H (J=18.5; H-22b); 2.45 d, 1H (J=18.8; H-22a); 2.42-2.52 m, 1H (ΣJ=40; H-16β); 2.68 dd, 1H (J$_1$=12.8, J$_2$=2.6; H-13β); 3.13-3.50 m, 6H (H-3α, H-20, H-5', H-3', H-4', H-2'); 3.75-3.87 m, 2H(H-6'a,b); 4.10-4.24 m, 2H(O—CH$_2$); 3.79 d, 1H (J=7, 6; H-1'). MS ESI m/z (%): [For C$_{38}$H$_{60}$O$_9$, M$^+$ 660], 683 ([M+Na]$^+$, 60). Elemental analysis for C$_{38}$H$_{60}$O$_9$: calculated C, 66.06%, H, 9.15%; found C, 66.39%, H, 8.98%.

Example 8

Preparation of Bisglucoside 7e, 7f (Method H-3)

i) To a suspension of the diol 7a (2.00 g; 3.92 mmol) in dry acetonitrile (25 ml), 2,3,4,6-tetraacetyl-α-D-glucopyranosyl bromide (6.4 g; 15.7 mmol) and mercury(II) cyanide (3.0 g; 11.8 mmol) were added and the mixture was then refluxed under a reflux condenser with the exclusion of air moisture. The course of the reaction was monitored by TLC (toluene/ether 6:1). The cooled-down reaction mixture was then bubbled through with moisted hydrogen sulphide, filtered through diatomaceous earth, the filtrate was diluted by tenfold excess of water and extracted into ethyl acetate. The combined organic extracts were shaken with water three times, dried by magnesium sulphate and the solvents were evaporated on a rotary vacuum evaporator. The evaporate was purified by column chromatography on silica gel, the mobile phase being toluene with gradient diethyl ether. The obtained acetylated bisglucoside 7d (2.50 g; 54%) had m.p. 102.7° C., [α]$_D$=+14° (c=0.28). IR spectrum: 1234 (C—O); 1603 (C=C); 1755 (C=O). $^1$H NMR spectrum: 0.73 s, 3H; 0.87 s, 3H; 0.89 s, 3H; 0.90 s, 3H, 1.09 s, 3H (5×CH$_3$); 1.99 s, 3H, 2.01 s, 3H, 2.02 s, 3H, 2.02 s, 3H, 2.03 s, 3H, 2.03 s, 3H, 2.04 s, 3H, 2.08 s, 3H (8×CH$_3$COO); 2.38 dt, 1H (J$_1$=14.0, J$_2$=4.9; H-16α); 3.58 dd, 1H (J$_1$=11.8, J$_2$=3.5; H-13β); 3.07 dd, 1H (J$_1$=11.6, J$_2$=4.9; H-3α); 3.51 m, 1H (ΣJ=16.8; H-5'); 3.67 m, 1H (ΣJ=17.7; H-5'); 3.99 d, 1H (J=11.0; H-28a); 4.11 m, 2H (H-6'a,b); 4.20 d, 1H (J=10.7; H-28b); 4.25 m, 2H(H-6'a,b); 4.53 d, 1H (J=7.9; H-1'); 4.63 d, 1H (J=8.2; H-1'); 4.89 dd, 1H (J$_1$=90.5, J$_2$=7.9; H-3'); 5.03 m, 1H (ΣJ=24.0; H-3'); 5.07-5.16 m, 3H (2×H-2'); 5.17-5.23 m, 2H (2×H-4'); 5.19 bs, 2H (Bn); 7.37 m, 5H (Ph). MS ESI m/z (%): [Pro C$_{60}$H$_{82}$O$_{23}$, M$^+$ 1170], 1193 ([M+Na]$^+$, 60). Elemental analysis for C$_{60}$H$_{82}$O$_{23}$: calculated C. 61.53%, H, 7.06%; found C, 63.86%, H, 7.52%.

ii) The obtained acetylated bisglucoside 7d (2.30 g; 1.97 mmol) was mixed with dry methanol (250 ml) and metal sodium (10 mg) was added into the mixture. The course of the reaction was monitored by reverse TLC (water/THF 1:1). The reaction mixture was then acidified with acetic acid to reach pH 6 and evaporated on a rotary vacuum evaporator. To the evaporate, water was added and the resulting suspension was filtered and washed with water. The precipitate was dried in exsiccator over phosphorus(V) oxide. The obtained bisglucoside 7e (1.36 g; 54%) had m.p. 186° C., [α]$_D$=+5° (c=0.33). IR spectrum (measured by the ATR technique): 1034, 1076 (C—O); 1708, 1726 (C=O); 3403 (O—H). $^1$H NMR spectrum: 0.84 s, 3H; 0.89 s, 3H; 0.93 s, 3H, 1.02 s, 3H, 1.12 s, 3H (5×CH$_3$); 2.39 dt, 1H (J$_1$=13.0, J$_2$=3.7; H-16α); 2.71 d, 1H (J=9.0; H-13β); 3.17m, 1H(H-3α); 3.24-3.34 m, 4H (2×H-5', 2×H-2'); 3.36-3.48 m, 4H(H-3', H-4'); 3.68-3.80 m, 2H(H-6'a,b); 3.84 m, 2H(H-6'a,b); 3.94 d, 1H (J=9.8; H-28a); 4.30 d, 1H (J=10.0; H-28b); 4.33 d, 1H (J=7.6; H-1'); 4.34 d, 1H (J=7.6; H-1') 5.20 bs, 2H (Bn); 7.35 m, 5H (ΣJ=3.2; Ph). $^{13}$C NMR spectrum is shown in Table 3. MS ESI m/z (%): [For C$_{44}$H$_{66}$O$_{15}$, M$^+$ 834], 858 ([M+Na]$^+$, 40). Elemental analysis for C$_{44}$H$_{66}$O$_{15}$: calculated C, 63.29%, H, 7.97%; found C, 63.44%, H, 7.52%.

ii) The bisglucoside 7e (1., 10 g; 1.32 mmol) was dissolved in the mixture of THF (10 ml) and methanol (10 ml) and the benzyl group was deprotected in an autoclave at the presence of Pd/C (100 mg; 10%) under hydrogen overpressure (0.6 MPa) while stirring. The course of the reaction was monitored by reverse TLC (water/THF 1:1). After 24 hours, the autoclave was opened and the reaction mixture was filtered through diatomaceous earth column. The eluate was evaporated on a rotary vacuum evaporator and the evaporate was recrystallized from methanol. The obtained bisglucosidic acid 7f (785 mg; 42%) had m.p. 194° C., [α]$_D$=+19 (c=0.31). IR spectrum (measured by the ATR technique): 1033, 1079 (C—O); 1693, 1707 (C=O); 3386 (O—H). $^1$H NMR spectrum: 0.85 s, 3H; 0.93 s, 3H; 0.96 s, 3H, 1.05 s, 3H, 1.18 s, 3H (5×CH$_3$); 2.32-2.45 m, 1H (H-16α); 2.87 dd, 1H (J$_1$=11.2, J$_2$=2.8; H-13β); 3.11-3.15 m (ΣJ=17.2; H-3α); 3.15-3.22 m, 4H, 3.24-3.30 m, 4H, 3.65 d, 2H (J=4.7; 2×H-6'a); 3.68 d, 2H (J=4.9; 2×H-6'b); 3.85 d, 1H (J=12.4; H-28a); 4.29 d, 2H (J=8.1; H-1'); 4.31 d, 1H (J=13.7; H-28b); 4.32 d, 1H (J=7.7; H-1'). MS ESI m/z (%): [Pro C$_{37}$H$_{60}$O$_{15}$, M$^+$ 734], 767 ([M+Na]$^+$, 40). Elemental analysis for C$_{37}$H$_{60}$O$_{15}$: calculated C, 59.66%, H, 8.12%; found C, 59.93%, H, 8.01%.

Example 9

Preparation of 2-Deoxygalactoside 4 k (Method H-4)

i) Into a solution of the triterpenic hydroxyderivative 4g (500 mg; 1.0 mmol) in dry acetonitrile (30 ml), tri-O-acetyl-galactal (1.2 mmol), molecular sieve 4 A (500 mg), lithium bromide (730 mg) and dried cation exchange resin in H$^+$ cycle (900 mg) were added. The reaction mixture was stirred at room temperature for 12 hours. The course of the reaction was monitored by thin-layer chromatography, the mobile phase being hexane:ethyl acetate 2:1. The reaction mixture was then filtered through a diatomaceous earth layer and the column was then washed with ethyl acetate. The reaction mixture was diluted with water (50 ml), extracted with ethyl acetate (2×20 ml) and the organic phase was evaporated on a rotary vacuum evaporator. The evaporate was dissolved in chloroform (5 ml) and the solution was poured over a short column of silica gel (elution with ethyl acetate). The eluate was evaporated on a rotary vacuum evaporator. The crude product was then separated by column chromatography on silica gel, elution with toluene. The product was then lyophilized from 2-methylpropan-2-ol, white lyophilizate was obtained 4j (360 mg; 47%) having melting point 100.8° C., $[\alpha]_D$=+38.9° (c=0.52).

ii) 2-deoxygalactoside 4j (200 mg; 0.26 mmol) was dissolved in dry methanol (300 ml) and catalytic amount of sodium (5 mg) was added into the solution. The course of the reaction was monitored by thin-layer chromatography on reverse phase (mobile phase water/tetrahydrofurane 1:1). The reaction mixture was neutralized with acetic acid and evaporated on a rotary vacuum evaporator. To the evaporate, water (300 ml) was added and the yielded precipitate of the product was filtered off. The filtration cake was washed with water. Obtained was white crystalline 2-deoxyglucoside 4 k (161 mg; 97%) having melting point of 158.0° C. and $[\alpha]_D$=+17.2° (c=0.51).

Example 10

Preparation of 2-Deoxyglucoside 4m (Method H-4)

i) Into a solution of the triterpenic hydroxyderivative 4d (500 mg; 1.0 mmol) in dry acetonitrile (30 ml), tri-O-acetylglucal (1.2 mmol), molecular sieve 4 A (500 mg), lithium bromide (730 mg) and dried cation exchange resin in H⁺ cycle (900 mg) were added. The reaction mixture was stirred at room temperature for 12 hours. The course of the reaction was monitored by thin-layer chromatography, the mobile phase being hexane:ethyl acetate 2:1. The reaction mixture was then filtered through a diatomaceous earth layer, and the column was washed with ethyl acetate. The reaction mixture was diluted with water (50 ml), extracted with ethyl acetate (2×20 ml) and the organic phase was evaporated on a rotary vacuum evaporator. The evaporate was dissolved in chloroform (5 ml) and the solution was poured over a short column of silica gel (elution with ethyl acetate). The eluate was evaporated on a rotary vacuum evaporator. The crude product was then separated by column chromatography on silica gel, eluted with toluene. The product was then lyophilized from 2-methylpropan-2-ol, obtained was white lyophilizate 4l (245 mg; 34%), melting point 204.1° C., $[\alpha]_D$=+24.2 (c=0.43).

ii) 2-deoxyglucoside 4l (60 mg; 0.08 mmol) was dissolved in dry methanol (100 ml) and a catalytic amount of sodium (5 mg) was added into the solution. The course of the reaction was monitored by thin-layer chromatography on reverse phase (mobile phase water:tetrahydrofurane 1:1). The reaction mixture was neutralized with acetic acid and evaporated on a rotary vacuum evaporator. To the evaporate, water (100 ml) was added and the yielded precipitate of the product was filtered off. The filtration cake was washed with water. Obtained was white crystalline 2-deoxyglucoside 4m (39 mg; 74%) having the melting point of 208.0° C., $[\alpha]_D$=+14.0 (c=0.40). $^{13}$C NMR spectrum: 15.7, 16.1, 16.5, 16.6, 18.0, 19.7, 19.8, 21.0, 21.6, 24.9, 27.5, 28.3, 28.9, 33.5, 34.7, 37.0, 37.6, 38.2, 38.3, 41.1, 45.1, 45.2, 47.4, 50.9, 52.4, 53.0, 55.4, 62.7, 68.6, 71.2, 72.1, 81.4, 93.1, 174.9, 145.5, 172.7, 208.0. MS m/z (%): [For $C_3H_{58}O_8$, M⁺ 630], 653 ([M+Na]⁺, 30), 631 ([M+H]⁺, 30). For $C_{37}H_{58}O_8$ (630.9) calculated: C, 70.44%, H, 9.27%. Found: C, 70.58%, H, 9.13%.

Example 11

Preparation of Glycolate 4a (Method K-1)

i) To a mixture of 21-oxoacid 4 (500 mg; 0.98 mmol) and potassium carbonate (276 mg; 2.0 mmol) in dichlormethane (10 ml) and acetonitrile (5 ml), benzyl bromoacetate (240 μl; 1.5 mmol) was added and the reaction mixture was stirred at room temperature for 24 h. The course of the reaction was monitored by TLC (toluene/diethyl ether 6:1). The reaction mixture was diluted with ten-fold excess of water and extracted into dichloromethane. The combined organic phases were shaken once with 5% HCl, three times with water, dried with magnesium sulphate and the solvents were evaporated on a rotary vacuum evaporator. The evaporate was purified by column chromatography on silica gel, the mobile phase being toluene. The obtained crude 21-oxoacid benzyl glycolate (509 mg; 79%) was used in the next step.

ii) Into a solution of 21-oxoacid benzyl glycolate (350 mg; 0.5 mmol) in the mixture of tetrahydrofurane (20 ml) and methanol (10 ml), palladium on carbon (75 mg; 10%) and 1,4-cyclohexadiene (473 μl; 5 mmol) were added and the reaction mixture was stirred at room temperature for 20 h. The course of the reaction was monitored using TLC (toluene/diethyl ether 4:1). The reaction mixture was then filtered through diatomaceous earth and the eluate was evaporated on a rotary vacuum evaporator. By the crystallization of the evaporate from the mixture of acetone/water, 21-oxoacid glycolate 4a (272 mg; 90%) having m.p. 267-269° C., $[\alpha]_D$=−33° (c=0.39) was obtained. $^{13}$C NMR spectrum: 15.9, 16.5, 16.6, 16.8, 18.1, 20.0, 20.1, 21.2, 21.3, 27.7, 29.0, 23.6, 25.1, 27.9, 33.5, 34.9, 37.1, 37.7, 38.5, 41.4, 45.3, 45.3, 47.3, 51.1, 53.1, 55.4, 60.4, 80.8, 146.0, 171.2, 171.7, 172.4, 173.7, 208.0. MS, m/z (%): [For $C_{34}H_{50}O_7$, M⁺ 570], 570 (M⁺, 18), 527 (5), 510 (22), 495 (6), 467 (23), 375 (4), 359 (3), 320 (16), 307 (98), 229 (10), 203 (31), 189 (52). For $C_{34}H_{50}O_7$ (570.4) calculated: 71.55% C, 8.83% H; found: 71.52% C, 8.85% H.

Example 12

Preparation of Glycolate 7d (Method K-1)

i) To a mixture of pentanoracid 7 (600 mg; 1.2 mmol), silver carbonate (440 mg; 1.6 mmol) in a mixture of chloroform (10 ml) and acetonitrile (7 ml), benzyl bromacetate (260 μl; 1.6 mmol) was added and the reaction mixture was stirred for 28 hours at room temperature. The course of the reaction was monitored by TLC (toluene/diethyl ether 6:1). The reaction mixture was then filtered through diatomaceous earth and the filtrate was worked-up and the product was purified by analogical procedure as in the preparation of 21-oxoacid benzyl glycolate. The obtained crude pentanoracid benzyl glycolate (358 mg; 46%) having m.p. 156-157° C. (methanol), $[\alpha]_D$=+57° (c=0.31) was used in the next step.

ii) Into a solution of pentanoracid benzyl glycolate (300 mg; 0.5 mmol) in a mixture of tetrahydrofurane (10 ml) and methanol (3 ml), palladium on carbon (75 mg; 10%) was added and the reaction mixture was hydrogenated with hydrogen in an autoclave under stirring at room temperature for 5 h. The course of the reaction was monitored by TLC (chloroform). The reaction mixture was then filtered through diatomaceous earth and the eluate was evaporated on a rotary vacuum evaporator. By crystallization of the evaporate from the mixture acetone/water, glycolate 7d (215 mg; 83%) having m.p. 230-230° C., $[\alpha]_D$=66° (c=0.23) was obtained. $^{13}$C NMR spectrum: 16.0, 16.2, 16.5, 16.7, 18.1, 19.7, 20.7, 21.3, 21.8, 23.6, 26.5, 27.1, 27.9, 34.0, 37.1, 37.8, 38.5, 41.0, 46.7, 50.5, 50.4, 55.4, 61.0, 63.2, 80.6, 170.2, 170.7, 171.0, 171.2, 210.5. MS, m/z (%): [For $C_{31}H_{46}O_9$, M⁺ 562], 562 (M⁺, 1), 516 (36), 502 (38), 487 (18), 459 (19), 415 (10), 339 (8), 313

(54), 223 (11), 204 (15), 189 (70). For $C_{31}H_{49}O_9$ (562.3) calculated: 66.17% C, 8.24% H; found: 66.24% C, 8.31% H.

Example 13

Preparation of Quarternary Ammonium Salt 2f (Method K-2)

i) To a suspension of betulinic acid 2 (1.37 g; 3 mmol) in a mixture of dichloromethane (15 ml) and acetonitrile (1 ml), potassium carbonate (0.42 g; 3 mmol) and 1,2-dibromoethane (550 ul; 4.5 mmol) were added and the reaction mixture was stirred at room temperature. The course of the reaction was monitored by TLC (toluene/ether 6:1). When all the reagent was consumed, the base was removed by filtration, the mixture was diluted with ten-fold excess of water and extracted into ethyl acetate. Combined organic phases were shaken three times with 5% HCl, three times with water, dried with magnesium sulphate and the solvents were evaporated on a rotary vacuum evaporator. The evaporate was purified by column chromatography on silica gel (ethyl acetate gradient in hexane). The obtained 2'-bromoethyl betulinate (480 mg; 28%) had m.p. 184° C., $[\alpha]_D$=+7° (c=0.24).

ii) 2'-bromoethyl betulinate (200 mg; 0.35 mmol) was dissolved in DMF (5 ml). To the solution, trimethylamine (0.5 ml; 5.67 mmol) was added, the reaction vessel was sealed and left at 60° C. for 1 h. After cooling, the reaction mixture was diluted with ten-fold excess of water and extracted into ethyl acetate. Combined organic phases were shaken three times with 5% HCl, three times with water, dried with magnesium sulphate and the solvents were evaporated on a rotary vacuum evaporator. The evaporate was purified by column chromatography on silica gel (methanol gradient in chloroform). The obtained quarternary ammonium salt 2f (163 mg; 75%) had m.p. 155-156° C., $[\alpha]_D$=+22° (c=0.40). $^{13}$C NMR spectrum: 15.1, 16.1, 16.6, 16.7, 19.3, 19.5, 21.9, 26.6, 27.9, 28.6, 30.8, 31.3, 32.7, 35.4, 37.5, 38.2, 39.3, 39.8, 39.9, 41.8, 43.4, 50.5, 51.8, 54.4, 56.6, 57.7, 58.4, 59.5, 65.9, 78.7, 79.1, 79.4, 79.5, 110.5, 128.1, 137.3, 151.2, 176.1. Elemental analysis for $C_{35}H_{60}BrNO_3$: calculated C, 67.50%, H, 9.71%; found C, 67.46%, H, 9.68%.

Example 14

Preparation of Quarternary Ammonium Salt 2g (Method K-2)

2'-bromoethyl betulinate prepared in Example 12 (285 mg; 0.46 mmol) was dissolved in DMF (5 ml), pyridine (1 ml; 9.49 mmol) was added to the solution, the reaction vessel was sealed and left at 60° C. for 4 days. After cooling, the reaction mixture was diluted with ten-fold excess of water and extracted into ethyl acetate. Combined organic phases were shaken three times with 5% HCl, three times with water, dried with magnesium sulphate and the solvents were evaporated on a rotary vacuum evaporator. The evaporate was purified by column chromatography on silica gel (methanol gradient in chloroform). The obtained quarternary ammonium salt 2g (527 mg; 86%) had m.p. 186-187° C., $[\alpha]_D$=+45° (c=0.39). $^{13}$C NMR spectrum: 15.0, 16.1, 16.7, 16.7, 19.4, 19.4, 21.9, 26.6, 28.0, 28.6, 30.8, 31.4, 32.7, 35.5, 37.5, 38.2, 39.5, 39.9, 40.0, 41.8, 43.4, 50.6, 51.8, 56.7, 57.9, 61.5, 63.6, 79.5, 79.5, 110.5, 129.7, 146.6, 147.7, 151.4, 176.3. Elemental analysis for $C_{37}H_{56}BrNO_3$: calculated C, 69.14% H, 8.78%; found C, 69.18%, H, 18.76%.

Example 15

Preparation of Quarternary Ammonium Salt 4o (Method K-2)

i) Into a suspension of acid 4 (5.0 g; 10 mmol) in the mixture of dichloromethane (150 ml) and acetonitrile (5 ml), potassium carbonate (2g; 14.2 mmol) and 1,2-dibromoethane (1.65 ml; 13.5 mmol) were added and the reaction mixture was stirred at room temperature. The course of the reaction was monitored by TLC (toluene/ether 6:1). After all the reactant was consumed, the base was removed by filtration, the mixture was diluted with ten-fold excess of water and extracted into ethyl acetate. Combined organic phases were shaken three times with 5% HCl, three times with water, dried by magnesium sulphate and the solvents were evaporated on a rotary vacuum evaporator. The evaporate was purified by column chromatography on silica gel (ethyl acetate gradient in hexane). The obtained 2'-bromoethylester of acid 4 (2.3 mg; 37%) had m.p. 210° C., $[\alpha]_D$=23° (c=0.35).

ii) The obtained 2'-bromoethylester of acid 4 (285 mg; 0.46 mmol) was dissolved in DMF (5 ml). To the solution, triethylamine (0.5 ml; 3.39 mmol) was added, the reaction vessel was sealed and left at 60° C. for 4 days. After cooling down, the reaction mixture was diluted with ten-fold excess of water and extracted into ethyl acetate. Combined organic phases were shaken three times with 5% HCl, three times with water, dried with magnesium sulphate and the solvents were evaporated on a rotary vacuum evaporator. The evaporate was purified by column chromatography on silica gel (methanol gradient in chloroform). The obtained quarternary ammonium ester 4o (68 mg; 19%) had m.p. 183° C., $[\alpha]_D$=+15° (c=0.31). $^{13}$C NMR spectrum: 16.4, 16.8, 17.2, 17.2, 18.7, 20.1, 21.4, 21.8, 24.2, 25.7, 28.3, 29.6, 29.8, 33.9, 35.5, 37.8, 38.4, 42.0, 45.9, 51.7, 53.9, 56.1, 65.3, 78.0, 78.3, 78.6, 81.9, 146.5, 172.5, 174.6, 209.1. Elemental analysis for $C_{40}H_{66}BrNO_5$: calculated C, 66.65%, H, 9.23%; found C, 66.66%, H, 9.26%.

Example 16

Preparation of Quarternary Ammonium Salt 4p (Method K-2)

2'-bromoethylester of acid 4 obtained in Example 14 (285 mg; 0.46 mmol) was dissolved in DMF (5 ml). To the solution, triethanolamine (500 mg; 4.7 mmol) was added, the reaction vessel was sealed and left at 60° C. for 10 days. After cooling down, the reaction mixture was diluted with ten-fold excess of water and extracted into ethyl acetate. Combined organic phases were shaken three times with 5% HCl, three times with water, dried with magnesium sulphate and the solvents were evaporated on a rotary vacuum evaporator. The evaporate was purified by column chromatography on silica gel (methanol gradient in chloroform). The obtained quarternary ammonium ester 4p (134 mg; 41%) had m.p. 162-163° C., $[\alpha]_D$=+28° (c=0.13). $^{13}$C NMR spectrum 16.5, 17.0, 17.3, 17.4, 19.2, 20.3, 20.6, 21.1, 22.4, 2.6, 26.4, 28.4, 28.8, 3.2, 34.5, 36.0, 38.3, 38.9, 39.6, 42.6, 46.0, 46.5, 46.8, 52.3, 54.3, 54.5, 56.7, 57.9, 60.8, 64.6, 79.5, 146.8, 172.8, 14.4, 15.5, 209.7. Elemental analysis for $C_{40}H_{66}BrNO_8$: calculated C, 62.49%, H, 8.65%; found C, 62.52%, H, 8.62%.

Example 17

Preparation of Hemiglutarate 2i (Method H-5)

Into a solution of methyl betulinate (2 h) (500 mg; 0.94 mmol) in 2,4,6-trimethylpyridine (10 ml), glutaric anhydride (1.15 g; 10 mmol) and DMAP (50 mg; 0.4 mmol) were added and the reaction mixture was refluxed while stirring for 8 hours. The course of the reaction was monitored by TLC (toluene/diethyl ether 2:1). The reaction mixture was then cooled down, diluted with ten-fold excess of water and extracted into ethyl acetate. Combined organic phases were shaken three times with 5% HCl, three times with water, dried with magnesium sulphate and the solvents were evaporated on a rotary vacuum evaporator. The evaporate was purified by column chromatography on silica gel by gradient elution from 8% ethyl acetate in hexane to 25% ethyl acetate in hexane. By crystallization from 2,2,4-trimethylpentane hemiglutarate 21 (386 mg; 62%) was obtained in the form of white crystals having m.p. 165° C., $[\alpha]_D$+17.5 (c 0.32). IR spectrum: 1230 (C—O), 1641 (C=C), 1716 (C=O), 2430-3500 (COOH), 3521 (O—H). $^1$H NMR spectrum: 0.83 s, 3H; 0.83 s, 3H; 0.84 s, 3H; 0.91 s, 3H; 0.96s, 3H, 1.69 s, 3H, (6×CH$_3$); 1.87-1.90 m, 2H, 1.92-2.00 pentet, 2H (J=7.2 Hz, H-33); 2.16-2.25 m, 2H, 2.37-2.41 t, 2H (J=7.3 Hz, H-32); 2.41-2.45 t, 2H (J=7.3 Hz, H-34); 3.00 m, 1H, 3.67 s, 3H(OCH$_3$); 4.46-4.50 m, 1H(H-3α); 4.60 s, 1H (H-29 pro-E); 4.73 s, 1H(H-29 pro-Z). $^{13}$C NMR spectrum: 14.68, 15.94, 16.16, 16.54, 18.18, 19.34, 20.00, 20.89, 23.73, 25.46, 27.99, 29.66, 30.59, 32.16, 32.93, 33.64, 34.24, 36.96, 37.10, 37.82, 38.24, 38.36, 40.68, 42.38, 46.99, 49.45, 50.44, 51.25, 55.41, 56.55, 81.10, 109.61, 150.54, 172.62, 176.68, 178.27. MS, m/z (%): [Pro C$_{36}$H$_{56}$O$_6$, M$^+$ 584], 584 (M$^+$, 3), 569 (2), 552 (1), 524 (3), 509 (1), 466 (1), 452 (15), 437 (7), 409 (5), 393 (4), 273 (3), 262 (12), 249 (6), 233 (5), 215 (6), 203 (14), 189 (37). Elemental analysis for C$_{36}$H$_{56}$O$_6$: calculated C, 73.93%, H, 9.65%; found C, 73.79%, H, 9.81%.

Example 18

Preparation of Galactopyranosyl Ester 21 (Method K-3)

i) Into a solution of betulinic acid (2) (1.00 g; 2.2 mmol) in a mixture of acetone (40 ml) and acetonitrile (20 ml), potassium carbonate (350 mg; 2.5 mmol) and 2,3,4,6-tetraacetyl-α-D-galactopyranosyl bromide (1.60 g; 3.6 mmol) were added. The course of the reaction was monitored by TLC (toluene/ether 10:1). When all the starting material was consumed, the base potassium carbonate was removed by filtration, the mixture was diluted with ten-fold excess of water and extracted into ethyl acetate. Combined organic phases were shaken once with 5% HCl, three times with water, dried with magnesium sulphate and the solvents were evaporated on a rotary vacuum evaporator. The evaporate was purified by column chromatography on silica gel (ethyl acetate/hexane 1:4). The obtained 2',3',4',6'-tetraacetyl-α-D-galactopyranosyl betulinate 2 k (1.60 g; 93%) had m.p. 189-190° C. (2,2, 4-trimethylpentane), $[\alpha]_D$+3.3° (c 0.46, ethanol). IR spectrum: 1641 (C=C), 1752 (C=O), 3612 (O—H). $^1$H NMR spectrum: 0.75 s, 3H; 0.82 s, 3H; 0.90 s, 3H; 0.92 s, 3H; 0.96 s, 3H, 1.68 s, 3H; (6×CH$_3$); 2.00 s, 3H, 2.03 s, 3H, 2.04 s, 3H, 2.17 s, 3H; (4×CH$_3$COO); 2.95 td, 1H (J$_1$=11.2, J$_2$=4.9; H-19β); 3.18 dd, 1H (J$_1$=11.2, J$_2$=4.6; H-3α); 4.02-4.06 m, 1H(H-5'); 4.08-4.18 m, 2H(H-6'a, H-6'b); 4.60 bs, 1H(H-29 pro-E); 4.74 d, 1H (J=1.7; H-29 pro-Z); 5.11 dd, 1H (J$_1$=10.5, J$_2$=3.4; H-3'); 5.37 dd, 1H (J$_1$=10.5, J$_2$=8.3; H-2'); 5.43 d, 1H (J=3.4; H-4'); 5.65 d, 1H (J=8.5; H-1'). MS, m/z (%): [For C$_{44}$H$_{66}$O$_{12}$, M$^+$ 786], 786 (M$^+$, 0.5), 696 (1), 579 (1), 455 (8), 437 (7), 411 (20), 393 (11), 331 (100), 203 (26), 189 (12). Elemental analysis: for C$_{44}$H$_{66}$O$_{12}$ (786.5) calculated: 67.15% C, 8.45% H; found: 67.19% C, 8.51% H.

ii) 2',3',4,6'-tetraacetyl-α-D-galactopyranosyl betulinate 2 k (1.00 g; 1.3 mmol) was dissolved in dry methanol (40 ml) and a catalytic amount of sodium (5 mg) was added into the solution. The course of the reaction was monitored by thin-layer chromatography on reverse phase (mobile phase water:tetrahydrofurane 1:1). After one hour, the reaction mixture was neutralized with acetic acid and evaporated on a rotary vacuum evaporator. To the evaporate, water (100 ml) was added and the yielded precipitate of the product was filtered off. The filtration cake was washed with water. Obtained was galactopyranosyl ester 21 in the form of white powder (685 mg; 86%), m. p. 238-240° C. (chloroform), $[\alpha]_D$ 0° (c 0.39, ethanol). IR spectrum (KBr): 1641 (C=C), 1740 (C=O), 3200-3600 (O—H). $^1$H NMR spectrum: 0.75 s, 3H; 0.82 s, 3H; 0.93 s, 3H; 0.95 s, 3H; 0.98 s, 3H, 1.69 s, 3H; (6×CH$_3$); 1.88-2.04 m, 2H(H-21β, H-22β); 2.23-2.37 m, 2H(H-13β, H-16β); 3.00 td, 1H (J$_1$=10.4, J$_2$=4.6; H-19β); 3.16 t, 1H (J=7.8; H-3α); 3.57 dd, 1H (J$_1$=9.5, J$_2$=3.2; H-3'); 3.62-3.82 m, 4H(H-2', H-5', H-6'a, H-6'b); 3.97 d, 1H (J=2.9; H-4'); 4.60 s, 1H(H-29 pro-E); 4.73 s, 1H(H-29 pro-Z); 5.46 d, 1H (J=8.1; H-1'). MS, m/z (%): [For C$_{36}$H$_{58}$O$_8$, M$^+$ 618], 618 (M$^+$, not found), 592 (1), 531 (1), 456 (18), 438 (17), 412 (10), 395 (11), 327 (6), 248 (47), 207 (53), 189 (100). Elemental analysis: for C$_{36}$H$_{58}$O$_8$ (618.4) calculated: 67.87% C, 9.45% H; found: 67.79% C, 9.50% H.

Example 19

Preparation of 3',3'-dimethylhemiglutarate 4q (Method H-6)

Into a solution of ethyl ester 4 g (500 mg; 0.99 mmol) in 2,4,6-trimethylpyridine (10 ml), 3,3-dimethylglutaric anhydride (600 mg; 2.4 mmol) and DMAP (50 mg; 0.4 mmol) were added and the reaction mixture was refluxed while stirring for 8 hours. The course of the reaction was monitored by TLC (toluene/diethyl ether 5:1). The reaction mixture was then cooled down, diluted with ten-fold excess of water and extracted into ethyl acetate. Combined organic phases were shaken three times with 5% HCl, three times with water, dried with magnesium sulphate and the solvents were evaporated on a rotary vacuum evaporator. The evaporate was purified by column chromatography on silica gel by gradient elution from 8% ethyl acetate in hexane to 25% ethyl acetate in hexane. The chromatographically uniform dimethyl hemiglutarate 4q was lyophilized from tert-butylalcohol (375 mg; 59%). $^{13}$C NMR spectrum: 14.15, 15.91, 16.62, 16.76, 18.11, 19.93, 20.16, 21.25, 23.68, 23.83, 24.03, 25.10, 27.63, 29.08, 30.80, 32.70, 33.51, 33.84, 34.79, 35.41, 37.12, 37.67, 37.81, 38.53, 41.29, 45.12, 45.52, 47.61, 50.99, 52.98, 55.43, 61.01, 81.24, 145.67, 171.82, 172.41, 174.32, 175.87, 207.36.

Example 20

Preparation of 3',3'-dimethylhemisuccinate 4t (Method H-7*)

i) Into a solution of benzyl 3β-hydroxy-21-oxolup-18-en-28-oate (500 mg; 0.89 mmol) in 2,4,6-trimethylpyridine (10 ml), 2,2-dimethylsuccinic anhydride (500 mg; 2.3 mmol) and DMAP (50 mg; 0.4 mmol) were added and the reaction mixture was refluxed while stirring for 8 hours. The course of the reaction was monitored by TLC (toluene/diethyl ether 5:1). The reaction mixture was then cooled down, diluted with ten-fold excess of water and extracted into ethyl acetate. Combined organic phases were shaken three times with 5% HCl, three times with water, dried with magnesium sulphate and the solvents were evaporated on a rotary vacuum evaporator. The evaporate was purified by column chromatography on silica gel by gradient elution from 8% ethyl acetate in hexane to 25% ethyl acetate in hexane. The chromatographically uniform benzyl 3β-(3',3'-dimethylsuccinyloxy)-21-oxolup-18-en-28-oate was lyophilized from tert-butylalcohol (380 mg; 55%). $^{13}$C NMR spectrum: 15.85, 16.43, 16.50, 16.73, 18.04, 19.89, 20.25, 21.04, 23.52, 25.01, 25.10, 25.59, 27.54, 27.86, 28.87, 33.43, 34.77, 37.05, 37.69, 38.53, 40.44, 40.74, 41.19, 44.67, 45.05, 45.16, 47.41, 50.96, 52.91, 55.41, 66.52, 81.32, 128.34, 128.58, 135.80, 145.62, 170.92, 171.84, 173.89, 176.24, 207.30.

ii) Into a solution of benzyl 3β-(3',3'-dimethylhemisukcinyloxy)-21-oxolup-18-en-28-oate (380 mg; 0.55 mmol) in ethanol (10 ml) and tetrahydrofurane (THF) (10 ml), cyklohexadiene (200 µl; 2.14 mmol) and Pd/C (150 mg; 10%) were added and the reaction mixture was stirred for 48 hours at laboratory temperature. The course of the reaction was monitored by TLC (toluene/diethyl ether 5:1). The reaction mixture was then filteres through a paper filter and the solvents were evaporated on a rotary vacuum evaporator. The dimethyl succinate 4t was lyophilized from tert-butylalcohol (312 mg; 95%). $^{13}$C NMR spectrum: 15.85, 16.43, 16.50, 16.73, 18.04, 19.89, 20.25, 21.04, 23.52, 25.01, 25.10, 25.59, 27.54, 27.86, 28.87, 33.43, 34.77, 37.05, 37.69, 38.53, 40.44, 40.74, 41.19, 44.67, 45.05, 45.16, 47.41, 50.96, 52.91, 55.41, 81.32, 170.92, 171.84, 173.89, 176.24, 207.30.

Example 21

Preparation of Hemitetrahydrophthalate 2m (Method H-8)

Into a solution of methyl betulinate (2 h) (500 mg; 0.94 mmol) in 2,4,6-trimethylpyridine (10 ml), cis-1,2,3,6-tetrahydrophthalic anhydride (760 mg; 5 mmol) and DMAP (50 mg; 0.4 mmol) were added and the reaction mixture was refluxed while stirring for 8 hours. The course of the reaction was monitored by TLC (toluene/diethyl ether 5:1). The reaction mixture was then cooled down, diluted with ten-fold excess of water and extracted into ethyl acetate. Combined organic phases were shaken three times with 5% HCl, three times with water, dried with magnesium sulphate and the solvents were evaporated on a rotary vacuum evaporator. The evaporate was purified by column chromatography on silica gel by gradient elution from 8% ethyl acetate in hexane to 25% ethyl acetate in hexane. By crystallization from isooctane, hemitetrahydrophthalate 2m (510 mg; 78%) was obtained in the form of white crystals having m.p. 224° C., $[\alpha]_D$+9.5 (c 0.32). IR spectrum: 1235 (C—O), 1641 (C═C), 1716 (C═O), 2250-3490 (COOH), 3512 (O—H). $^1$H NMR spectrum: 0.80 s, 3H; 0.81 s, 3H; 0.83 s, 3H; 0.91 s, 3H; 0.96 s, 3H, 1.69 s, 3H, (6×CH$_3$); 1.84-1.93 m, 2H, 2.18-2.25 m, 2H, 2.33-2.66 m, 4H(H-33, H-36); 3.00 m, 1H, 3.07-3.15 m, 2H(H-32, H-37); 3.67 s, 3H(OCH$_3$); 4.47-4.53 m, 1H(H-3α); 4.60 s, 1H(H-29 pro-E); 4.73 s, 1H (H-29 pro-Z); 5.69 d, 2H (J=7.6 Hz, H-34, H-35). $^{13}$C NMR spectrum: 14.69, 15.94, 16.11, 16.51, 18.14, 19.33, 20.89, 23.51, 25.31, 25.45, 26.34, 27.80, 29.65, 30.58, 32.15, 34.22, 36.94, 37.08, 37.86, 38.23, 38.36, 39.67, 39.90, 40.68, 42.38, 46.98, 49.44, 50.40, 51.24, 55.43, 56.54, 81.61, 109.61, 125.11, 125.39, 150.54, 172.81, 176.66, 178.84. MS, m/z (%): [Pro C$_{39}$H$_{58}$O$_6$, M$^+$ 622], 622 (M$^+$, 4), 607 (2), 579 (1), 562 (5), 452 (52), 437 (17), 409 (13), 393 (15), 273 (6), 262 (25), 249 (14), 233 (7), 215 (13), 203 (41), 189 (100). Elemental analysis: for C$_{39}$H$_{58}$O$_6$ (622) calculated: C, 75.20%, H, 9.39%; found: C, 75.08%, H, 9.48%.

Example 22

Preparation of Hemidiglycolate 4x (Method H-9)

Into a solution of ethyl ester 4 g (500 mg; 0.99 mmol) in 2,4,6-trimethylpyridine (10 ml), diglycolic anhydride (500 mg; 2.3 mmol) and DMAP (50 mg; 0.4 mmol) were added and the reaction mixture was refluxed while stirring for 8 hours. The course of the reaction was monitored by TLC (toluene/diethyl ether 5:1). The reaction mixture was then cooled down, diluted with ten-fold excess of water and extracted into ethyl acetate. Combined organic phases were shaken three times with 5% HCl, three times with water, dried with magnesium sulphate and the solvents were evaporated on a rotary vacuum evaporator. The evaporate was purified by column chromatography on silica gel by gradient elution from 8% ethyl acetate in hexane to 25% ethyl acetate in hexane. The chromatographically uniform diglycolate 4x was lyophilized from tert-butylalcohol (406 mg; 66%). $^{13}$C NMR spectrum: 14.16, 15.92, 16.51, 16.62, 16.77, 18.12, 19.98, 20.15, 21.30, 23.57, 25.13, 26.38, 27.48, 27.62, 28.04, 29.09, 29.68, 33.50, 34.77, 37.09, 37.86, 38.51, 41.29, 45.10, 47.61, 51.01, 52.96, 55.36, 61.05, 145.66, 171.66, 172.58, 174.27, 175.43, 207.27.

b) Preparation of Inclusion Compound

Method A: In a mixture of water (26.0 ml), sodium hydrogencarbonate solution (5.0 ml; saturated solution) and ethanol (7.0 ml; 99%), 2-hydroxypropyl-γ-cyklodextrin (10.0 g) is dissolved at the temperature of 50° C. under vigorous stirring. Into the resulting colourless, viscous solution, soluble triterpene derivative (1.50 g) is added at once and the mixture is again vigorously stirred at the temperature of 50° C. 20 to 40 min of stirring is usually necessary for a complete dissolution. After the triterpenoid is completely dissolved, the resulting clear solution is cooled to room temperature, filtered with a syringe filter (hydrophilic, pore size 0.22 µm) in order to be sterile and is placed in a refrigerator. The obtained solution can be stored in a freezer at −20° C. until further use without any perceptible decomposition.

Method B: In a mixture of water (14.0 ml) and propylene glycol (6.0 ml), 2-hydroxypropyl-γ-cyklodextrin (7.00 g) is dissolved at the temperature of 50° C. under vigorous stirring. Into the resulting colourless, viscous solution, soluble triterpene derivate (1.00 g) is added at once and is again vigorously stirred at the temperature of 50° C. 20 to 40 min of stirring is usually necessary for a complete dissolution. After the triterpenoid is completely dissolved, the resulting clear solution is cooled to room temperature, filtered with a syringe filter (hydrophilic, pore size 0.22 µm) in order to be sterile and is placed in a refrigerator. The obtained solution can be stored in a freezer at −20° C. until further use without any perceptible decomposition.

Determination of Bioavailability and Pharmacokinetic Profile at Oral Administration of the Compounds to Laboratory Mice Soluble cyclodextrin formulations of terpenoid compounds, prepared in accordance with the aforementioned methods A or B, were administered without dilution to outbred mice CD-1 intragastrically (200 µl in a single dose) as aqueous solutions by injection syringe equipped with a gastric tube. Insoluble compounds were administered intragastrically as well (200 µl in a single dose), but in the form of aqueous suspensions in 0.5-1% carboxymethyl cellulose. In time intervals 2, 4, 6, 8, 12 and 24 h, blood was taken from the mice, the blood was centrifuged and the obtained plasma was subsequently analysed by HPLC-ESI MS technique.

Analytic Determination of the Concentration of Dissolved Triterpenoids in the Application Form and in Plasma Samples HPLC-ESI MS technique was used or the determination of the concentration of dissolved triterpenoids. The samples were measured in one analytical batch with calibration solutions and blind control. The sample for the measurement was prepared from 50 µl of aqueous solution containing the inclusion compound by dilution with methanol to the volume of 10 ml. Subsequently, 10 µl of the sample solution after the first dilution is further diluted to 1 ml by the mobile phase. The blind control was obtained from 50 µl of pre-prepared aqueous solution of 2-hydroxypropyl-γ-cyklodextrin by dilution with methanol to 10 ml. Subsequently, 10 µl of the blind control solution after the first dilution is further diluted to 1 ml by methanol. Stock solutions of standards (concentration 0.2 mg/ml) were prepared by weighing 2.00 mg of analyte to 10 ml graduated flask and dissolution in methanol. The calibration samples were then prepared by dilution of the stock solution with mobile phase (0.4 µg/ml resp. 4 µg/ml).

The analysis was carried out at ODS Hypersil 125×2.1 mm, 5 um, SN 0745415X, Thermo EC column, ODS 4.0×3.0 mm precolumn, Phenomenex, mobile phase A—100 mmol/L aqueous solution of ammonium formate, pH is adjusted to 5 by formic acid, B—100 mmol/L methanolic solution of ammonium formate, column temperature: 25° C., linear gradient or isocratic elution, injected volume 30 µl. The concentration was determined by comparison with standard and calculated to the original solution containing the inclusion compound.

The pharmacokinetic profiles of selected derivatives at oral administration to mice (compounds 2b, 3, 3b, 5a, 5f, 6a, 8a, 4v, 4i, 2i, 4t were administered as cyclodextrin formulations, compounds 5c, 5d, 6, 7, 8 as carboxymethyl cellulose suspensions) are shown in FIG. 1 to 12. The results prove oral availability of the soluble cyclodextrin terpenoid formulations, but not of the insoluble suspensions.

TABLE 1

Examples of solubility of biologically active triterpenoids (n = concentration lower than the detection threshold, i.e. 1 ng/ml; months means two or more months)

| Reagent | Soluble derivative | | | |
|---|---|---|---|---|
| | Derivatiaztion method | Solution method | Conc. of dissolved substance mg/ml | Stability of the solution at −20° C. time |
| Betulin | — | B | n | — |
| Betulin 1/betulin dihemisuccinate 1a | H-1 | A | 54 | months |
| Betulin 1/betulin dihemiphtalate 1b | H-2 | A | 39 | months |
| Betulin 1/betulin diglucoside 1c | H-3 | B | 55 | months |
| Ethyl-betulinate 2a | — | B | n | — |
| Ethyl-betulinate 2a/hemisuccinate 2b | H-1 | A | 45 | months |
| Ethyl-betulinate 2a/hemiphtalate 2c | H-2 | A | 41 | months |
| Ethyl-betulinate 2a/glucoside 2d | H-3 | B | 43 | months |
| Betulinic acid 2 | — | A | 38 | months |
| Betulinic acid 2/hemisuccinate 2e | H-1* | A | 51 | months |
| Betulinic acid 2/ethyltrimethylammonium bromide-betulinate 2 | K-2 | B | 55 | months |
| Betulinic acid 2/ethylpyridinium bromide-betulinate 2g | K-2 | B | 31 | months |
| Methyl betulinate 2h | — | B | n | — |
| Methyl betulinate 2h/hemiglutarate 2i | H-5 | A | 51 | months |
| Betulinic acid 2/glucosyl ester 2j | K-3 | A/B | 59/70 | months |
| Betulinic acid 2/galactosyl ester 2l | K-3 | B | 44 | months |
| Betulinic acid 2/dimethylhemisuccinate 2n | H-7 | A | 61 | months |
| Methyl betulinate 2h/hemitetrahydrophthalate 2m | H-8 | A | 43 | months |
| Aldehyde 3 | — | A | 35 | months |
| Ethyl-ester 3a | — | B | n | — |
| Ethyl-ester 3a 3/hemisuccinate 3b | H-1 | A | 55 | months |
| Ethyl-ester 3a/hemiphtalate 3b | H-2 | A | 40 | months |
| 21-oxoacid 4 | — | A | 48 | months |
| 21-oxoacid 4/glycolate 4a | K-1 | A | 59 | months |
| 21-oxoacid 4/ethyltrimethylammonium bromide salt 4b | K-2 | B | 47 | months |
| 21-oxoacid 4/ethylpyridinium bromide salt 4c | K-2 | B | 33 | months |
| 21-oxoacid 4/ethyltriethylammonium bromide salt 4o | K-2 | B | 37 | months |
| 21-oxoacid 4/ethyltriethanolammoniumbromide salt 4p | K-2 | B | 41 | months |
| 21-oxoacid 4/dimethylhemisuccinate 4t | H-7* | A | 49 | months |
| 21-oxoacid 4/dimethylhemiglutarate 4u | H-6* | A | 44 | months |
| 21-oxoacid 4/glukosyl ester 4w | K-3 | B | 31 | months |
| Methyl-ester 4d | — | B | n | — |
| Ethyl-ester 4g/hemisuccinate 4e | H-1 | A | 53 | months |
| Ethyl-ester 4g/hemiphtalate 4f | H-2 | A | 28 | months |
| ethyl-ester 4g/glucoside 4i | H-3 | B | 56 | months |
| ethyl-ester 4g/2-deoxygalactoside 4j | H-4 | B | 60 | months |
| ethyl-ester 4g/dimethylhemiglutarate 4q | H-6 | A | 58 | months |
| ethyl-ester 4g/dimethylhemisuccinate 4r | H-7 | A | 44 | months |
| ethyl-ester 4g/hemidiglycolate 4x | H-9 | A | 44 | months |
| methyl-ester 4d/2-deoxyglucoside 4l | H-4 | B | 61 | months |

TABLE 1-continued

Examples of solubility of biologically active triterpenoids (n = concentration lower than the detection threshold, i.e. 1 ng/ml; months means two or more months)

| Reagent | Derivatiaztion method | Solution method | Conc. of dissolved substance mg/ml | Stability of the solution at −20° C. time |
|---|---|---|---|---|
| methyl-ester 4d/dimethylhemisuccinate 4s | H-7 | A | 44 | months |
| methyl-ester 4d/2-deoxygalactoside 4v | H-4 | B | 68 | months |
| Diketone 5 | — | B | n | — |
| diketone 5/diketone hemisuccinate 5a | H-1 | A | 50 | month |
| diketone 5/glucoside 5b | H-3 | B | 51 | months |
| diketone 5/diketone dihemisuccinate 5e | H-1 | A | 69 | months |
| diketone 5/dimethylhemisuccinate 5f | H-7 | A | 51 | month |
| diketone 5/dimethylhemiglutarate 5g | H-6 | A | 47 | month |
| diketone 5/2-deoxygalactoside 5h | H-4 | B | 63 | month |
| Pyrazine 6 | — | A | 1, 2 | months |
| pyrazine 6/pyrazine glycolate 6a | K-1 | A | 56 | months |
| pyrazine 6/ethyltrimethylethylammonium bromide salt 6b | K-2 | B | 49 | months |
| Pentanoracid 7 | — | A | 68 | week |
| pentanoracid 7/dihemisuccinate 7c | H-1* | A | 73 | month |
| pentanoracid 7/diglucoside 7f | H-3 | A/B | 72/79 m | onths |
| pentanoracid 7/glycolate 7d | K-1 | A | 75 | month |
| aminoalcohol 8/hemisuccinate 8a | H-1 | A | 37 | months |

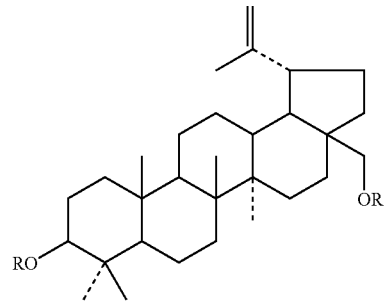

1, R = H
1a, R = CO(CH$_2$)$_2$CO$_2$H
1b, R = CO(C$_6$H$_4$)CO$_2$H
1c, R = 1β-D-glucosyl

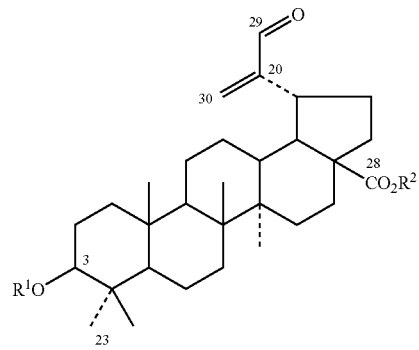

3, R$^1$ = R$^2$ = H
3a, R$^1$ = H, R$^2$ = CH$_2$CH$_3$
3b, R$^1$ = CO(CH$_2$)$_2$CO$_2$H, R$^2$ = CH$_2$CH$_3$
3c, R$^1$ = CO(C$_6$H$_4$)CO$_2$H, R$^2$ = CH$_2$CH$_3$

TABLE 1-continued

Examples of solubility of biologically active triterpenoids (n = concentration lower than the detection threshold, i.e. 1 ng/ml; months means two or more months)

| | Soluble derivative | | | |
|---|---|---|---|---|
| Reagent | Derivatiaztion method — | Solution method — | Conc. of dissolved substance mg/ml | Stability of the solution at $-20°$ C. time |

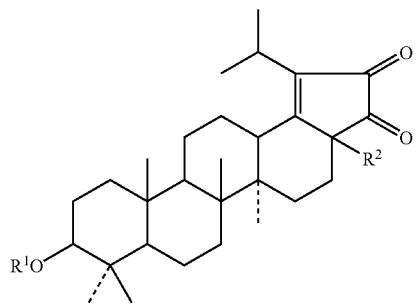

5, $R^1$ = H, $R^2$ = $CO_2CH_3$
5a, $R^1$ = $CO(CH_2)_2CO_2H$, $R^2$ = $CO_2CH_3$
5b, $R^1$ = 1β-D-glucosyl, $R^2$ = $CO_2CH_3$
5c, $R^1$ = Ac, $R^2$ = $CO_2CH_3$
5d, $R^1$ = H, $R^2$ = $CH_2OH$
5e, $R^1$ = $CO(CH_2)_2CO_2H$, $R^2$ = $CH_2OCO(CH_2)_2CO_2H$
5f, $R^1$ = $COCH_2C(CH_3)_2CO_2H$, $R^2$ = $CO_2CH_3$
5g, $R^1$ = $COCH_2C(CH_3)_2CH_2CO_2H$, $R^2$ = $CO_2CH_3$
5h, $R^1$ = 2-deoxy-1α-D-galactosyl, $R^2$ = $CO_2CH_3$

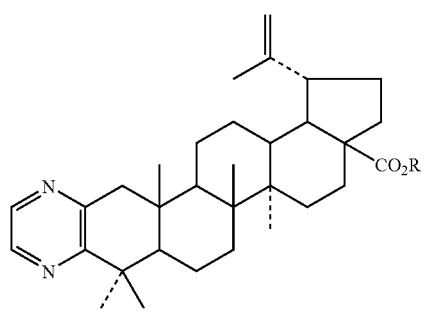

6, R = H
6a, R = $CH_2CO_2H$
6b, R = $(CH_2)_2N^+C_5H_5Br^-$

TABLE 1-continued

Examples of solubility of biologically active triterpenoids (n = concentration lower than the detection threshold, i.e. 1 ng/ml; months means two or more months)

| Reagent | Soluble derivative | | | |
|---|---|---|---|---|
| | Derivatiaztion method | Solution method | Conc. of dissolved substance mg/ml | Stability of the solution at −20° C. time |

8, $R^1 = R^2 = H$
8a, $R^1 = CO(CH_2)_2CO_2H$, $R^2 = H$

2, $R^1 = R^2 = H$
2a, $R^1 = H$, $R^2 = CH_2CH_3$
2b, $R^1 = CO(CH_2)_2CO_2H$, $R^2 = CH_2CH_3$
2c, $R^1 = CO(C_6H_4)CO_2H$, $R^2 = CH_2CH_3$
2d, $R^1 = 1\beta$-D-glucosyl, $R^2 = CH_2CH_3$
2e, $R^1 = CO(CH_2)_2CO_2H$, $R^2 = H$
2f, $R^1 = H$, $R^2 = (CH_2)_2N^+(CH_3)_3Br^-$
2g, $R^1 = H$, $R^2 = (CH_2)_2N^+C_5H_5Br^-$
2h, $R^1 = H$, $R^2 = CH_3$
2i, $R^1 = CO(CH_2)_3CO_2H$, $R^2 = CH_3$
2j, $R^1 = H$, $R^2 = 1\beta$-D-glucosyl
2k, $R^1 = H$, $R^2 = 2,3,4,6$-tetraacetyl-$1\beta$-D-galactosyl
2l, $R^1 = H$, $R^2 = 1\beta$-D-galactosyl
2m, $R^1 = COCHCH_2HC=CHCH_2CHCO_2H$, $R^2 = CH_3$
2n, $R^1 = COCH_2C(CH_3)_2CO_2H$, $R^2 = CH_3$ TABLE 1-continued Examples of solubility of biologically active triterpenoids (n = concentration lower than the detection threshold, i.e. 1 ng/ml; months means two or more months)

| Reagent | Soluble derivative | | | |
|---|---|---|---|---|
| | Derivatization method | Solution method | Conc. of dissolved substance mg/ml | Stability of the solution at −20° C. time |
| | — | — | | |

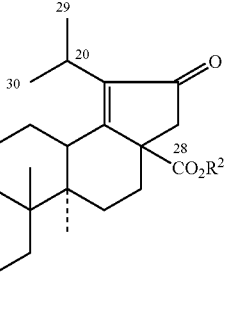

4, $R^1$ = Ac, $R^2$ = H
4a, $R^1$ = Ac, $R^2$ = $CH_2CO_2H$
4b, $R^1$ = Ac, $R^2$ = $(CH_2)_2N^+(CH_3)_3Br^-$
4c, $R^1$ = Ac, $R^2$ = $(CH_2)_2N^+C_5H_5Br^-$
4d, $R^1$ = H, $R^2$ = $CH_3$
4e, $R^1$ = $CO(CH_2)_2CO_2H$, $R^2$ = $CH_2CH_3$
4f, $R^1$ = $CO(C_6H_4)CO_2H$, $R^2$ = $CH_2CH_3$
4g, $R^1$ = H, $R^2$ = $CH_2CH_3$
4h, $R^1$ = 2,3,4,6-tetra-O-acetyl-1β-D-glucosyl, $R^2$ = $CH_2CH_3$
4i, $R^1$ = 1β-D-glucosyl, $R^2$ = $CH_2CH_3$
4j, $R^1$ = 3,4,6-tri-O-acetyl-2-deoxy-1α-D-galactosyl, $R^2$ = $CH_2CH_3$
4k, $R^1$ = 2-deoxy-1α-D-galactosyl, $R^2$ = $CH_2CH_3$
4l, $R^1$ = 3,4,6-tri-O-acetyl-2-deoxy-1α-D-glucosyl, $R^2$ = $CH_3$
4m, $R^1$ = 2-deoxy-1α-D-glucosyl, $R^2$ = $CH_3$
4o, $R^1$ = Ac, $R^2$ = $(CH_2)_2N^+(CH_2CH_3)_3Br^-$
4p, $R^1$ = Ac, $R^2$ = $(CH_2)_2N^+(CH_2CH_2OH)_3Br^-$
4q, $R^1$ = $COCH_2C(CH_3)_2CH_2CO_2H$, $R^2$ = $CH_2CH_3$
4r, $R^1$ = $COCH_2C(CH_3)_2CO_2H$, $R^2$ = $CH_2CH_3$
4s, $R^1$ = $COCH_2C(CH_3)_2CO_2H$, $R^2$ = $CH_3$
4t, $R^1$ = $COCH_2C(CH_3)_2CO_2H$, $R^2$ = H
4u, $R^1$ = $COCH_2C(CH_3)_2CH_2CO_2H$, $R^2$ = H
4v, $R^1$ = 2-deoxy-1α-D-galactosyl, $R^2$ = $CH_3$
4w, $R^1$ = Ac, $R^2$ = 1β-D-glucosyl
4x, $R^1$ = $COCH_2OCH_2CO_2H$, $R^2$ = $CH_2CH_3$

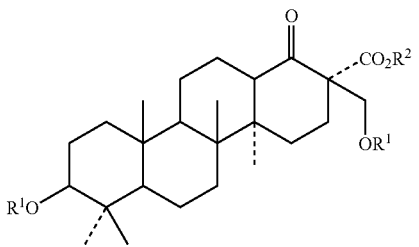

7, $R^1$ = Ac, $R^2$ = H
7a, $R^1$ = H, $R^2$ = $CH_2C_6H_5$
7b, $R^1$ = $CO(CH_2)_2CO_2H$, $R^2$ = $CH_2C_6H_5$
7c, $R^1$ = $CO(CH_2)_2CO_2H$, $R^2$ = H
7d, $R^1$ = 2,3,4,6-tetra-O-acetyl-1β-D-glucosyl, $R^2$ = $CH_2C_6H_5$
7e, $R^1$ = 1β-D-glucosyl, $R^2$ = $CH_2C_6H_5$
7f, $R^1$ = 1β-D-glucosyl, $R^2$ = H

The invention claimed is:
1. A method of preparation of a soluble formulation of water-insoluble pentacyclic and tetracyclic terpenoids, characterized in that the water-insoluble terpenoid having a free, hydroxy functional group is derivatized on this functional group with a substituent of general formula $X^a$ bound to the hydroxy group of the terpenoid, wherein $X^a$ is —OC—R—COOH, wherein R is linear or branched $C_1$ to $C_8$ alkylene, linear or branched $C_3$ to $C_8$ oxaalkylene, linear or branched $C_1$ to $C_8$ alkenylene, $C_6$ cycloalkylene, $C_6$ cycloalkenylene, $C_6$ arylene unsubstituted or substituted with halogen, hydroxyl or amino group, wherein the functionalized terpenoid is selected from:

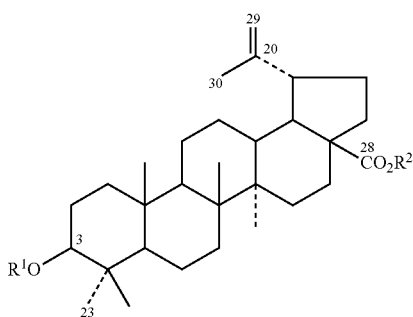

wherein $R^1$ is $X^a$ and $R^2$ is $CH_2CH_3$, $CH_3$ or H

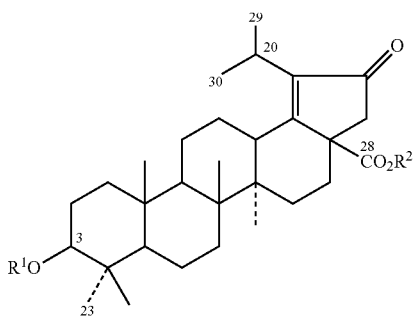

wherein $R^1$ is $X^a$ and $R^2$ is $CH_2CH_3$, $CH_3$ or H,

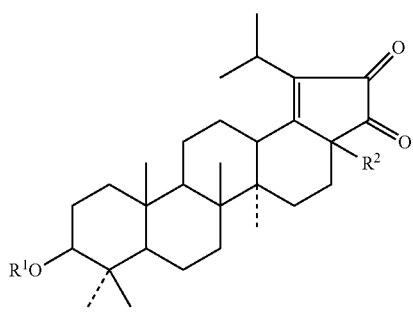

wherein $R^1$ is $X^a$ and $R^2$ is $CO_2CH_3$,
and subsequently, the prepared derivative is dissolved in a solution containing water, a gamma-cyclodextrin and optionally pharmaceutically acceptable auxiliary substances, forming an inclusion derivative with the gamma-cyclodextrin.

2. The method according to claim 1, characterized in that the substituents of general formula $X^a$ are selected from the group consisting of succinate, glutarate, 3',3'-dimethylglutarate, 3',3'-dimethylsuccinate, tetrahydrophthalate, diglycolate or phthalate.

3. A soluble formulation of a pentacyclic or tetracyclic terpenoid, containing an inclusion complex of the pentacyclic terpenoid selected from the group consisting of:

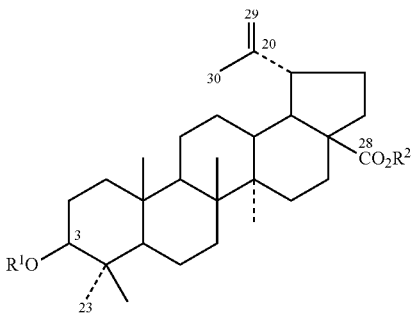

wherein $R^1$ is $X^a$ and $R^2$ is $CH_2CH_3$, $CH_3$ or H

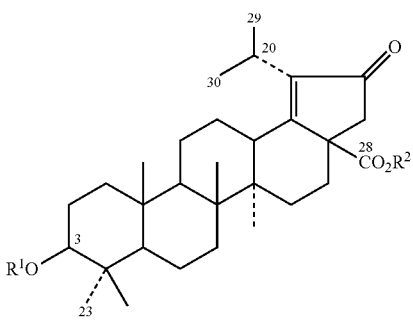

wherein $R^1$ is $X^a$ and $R^2$ is $CH_2CH_3$, $CH_3$ or H,

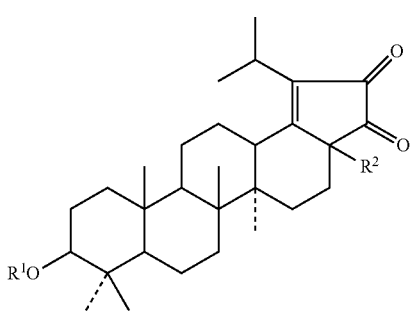

wherein $R^1$ is $X^a$ and $R^2$ is $CO_2CH_3$,
wherein $X^a$ is —OC—R—COOH, wherein $X^a$ is —OC—R—COOH, wherein R is linear or branched $C_1$ to $C_8$ alkylene, linear or branched $C_3$ to $C_8$ oxaalkylene, linear or branched $C_1$ to $C_8$ alkenylene, $C_6$ cycloalkylene, $C_6$ cycloalkenylene, $C_6$ arylene unsubstituted or substituted with halogen, hydroxyl or amino group;
with a gamma-cyclodextrin, and optionally water and pharmaceutically acceptable auxiliary substances.

4. The soluble formulation according to claim 3, characterized in that the substituents of general formula $X^a$ are selected from the group consisting of succinate, glutarate, 3',3'-dimethylglutarate, 3',3'-dimethylsuccinate, tetrahydrophthalate, diglycolate or phthalate.

5. A pharmaceutical composition, characterized in that it contains the soluble formulation according to claim 3 and a pharmaceutically acceptable solvent.

6. The pharmaceutical composition according to claim 3, characterized in that the pharmaceutically acceptable solvent is water.

* * * * *